United States Patent
Masuda et al.

(10) Patent No.: US 7,378,251 B2
(45) Date of Patent: May 27, 2008

(54) METHODS OF IDENTIFYING COMPOUNDS THAT MODULATE IL-4 RECEPTOR-MEDIATED IGE SYNTHESIS UTILIZING A THIOREDOXIN-LIKE 32 KDA PROTEIN

(75) Inventors: Esteban Masuda, Menlo Park, CA (US); Todd M. Kinsella, Fayetteville, NC (US); Justin E. Warner, San Fancisco, CA (US); Taisei Kinoshita, San Mateo, CA (US); Mark K. Bennett, Moraga, CA (US); David C. Anderson, San Bruno, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/197,962

(22) Filed: Jul. 16, 2002

(65) Prior Publication Data

US 2004/0014149 A1 Jan. 22, 2004

(51) Int. Cl.
*G01N 33/53* (2006.01)
(52) U.S. Cl. ..................................... 435/7.2
(58) Field of Classification Search ............... 435/7.1
See application file for complete search history.

(56) References Cited

U.S. PATENT DOCUMENTS 5,831,049 A * 11/1998 Hillman et al. ............ 536/23.1
5,958,707 A    9/1999 de Vries et al.
6,689,775 B2 * 2/2004 Powis ........................ 514/208

OTHER PUBLICATIONS

Chen X. et al., Crystallization and preliminary X-ray analysis of a Trx domain of human thioredoxin-like protein, ACTA Cryst. D57:1712-1714 (2001).
Lee K. et al., Purification, Molecular Cloning, and Characterization of TRP32, a Novel Thioredoxin-related Mammalian Protein of 32 kDa, The Journal of Biological Chemistry 273:30:19160-19166 (1998).
Miranda-Vizuete et al., Molecular Cloning and Expression of a cDNA Encoding a Human Thioredoxin-like Protein, Biochemical and Biophysical Research Communications 243:284-288 (1998).
Miranda-Vizuete et al., Identification of a Novel Thioredoxin-l Pseudogene on Human Chromosome 10, DNA Sequence 10(6):411-414 (2000).
Miranda-Vizuete et al., Genomic Structure and Chromosomal Localization of Human Thioredoxin-Like Protein Gene (txl) DNA Sequence 10(6): 419-424 (2000).
Miranda et al., 2000, Genomic Structure and Chromosomal Localization of Human Thioredoxin-Like Protein Gene (txl), *DNA Sequence* 10(6):419-424.
Databases Unisave, "Thioredoxin-like protein (32kDa thoredoxin-like protein)," Accession No. 043396 (Jun. 6, 2002).

* cited by examiner

*Primary Examiner*—Michael Pak
(74) *Attorney, Agent, or Firm*—James J. Diehl; James S. Keddie; Carol L. Francis

(57) ABSTRACT

The present provides compounds capable of modulating IL-4 receptor-mediated IgE production, as well as IL-4 induced processes associated therewith, methods and kits for identifying such compounds that utilize a thioredoxin-like 32 kDa protein (TXNL) as a surrogate analyte and methods of using the compounds in a variety of in vitro, in vitro and ex vivo contexts.

28 Claims, 12 Drawing Sheets

FIG. 1

Nucleotide Sequence of 603 bp Fragment of the Human Germline ε Promoter
(SEQ ID NO:6)

```
CTCGAGGACA  GTGACCTGGG  AGTGAGTACA  AGGTGAGGCC  ACCACTCAGG
GTGCCAGCTC  CAAGCGGGTC  ACAGGGACGA  GGGCTGCCGC  CATCAGGAGG
CCCTGCACAC  ACATCTGGGA  CACGCGCCCC  CGAGGGCCAG  TTCACCTCAG
TGCGCCTCAT  TCTCCTGCAC  AAAAGCGCCC  CCATCCTTTC  TTCACAAGGC
TTTCGTGGAA  GCAGAGGCGT  CGATGCCCAG  TACCCTCTCC  CTTTCCCAGG
CAACGGGACC  CCAAGTTTGC  TGACTGGGAC  CACCAAGCCA  CGCATGCGTC
AAGAGTGAGA  GTCCGGGACC  TAGGCAGGGG  CCCTGGGGTT  GGGCCTGAGA
GAGAAGAGAA  CCTCCCCCAG  CACTCGGTGT  GCATCGGTAG  TGAAGGAGCC
TCACCTGACC  CCCGCTGTTG  CTCAATCGAC  TTCCCAAGAA  CAGAGAGAAA
AGGGAACTTC  CAGGGCGGCC  CGGGCCTCCT  GGGGGTTCCC  ACCCCATTTT
TAGCTGAAAG  CACTGAGGCA  GAGCTCCCCC  TACCCAGGCT  CCACTGCCCG
GCACAGAAAT  AACAACCACG  GTTACTGATC  ATCTGGGAGC  TGTCCAGGAA
TTC
```

FIG. 2A
The DT Toxin Selection of the A5T4 Reporter Line

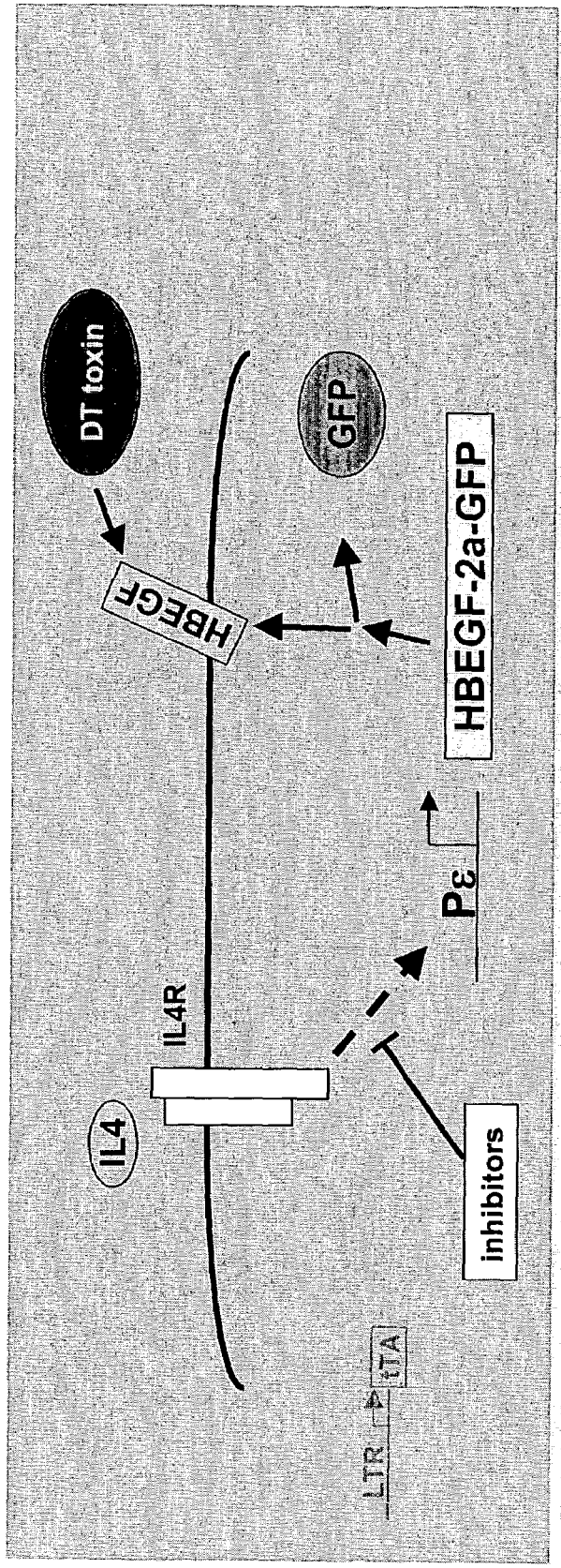

- The A5T4 cell line generated has a dual-function reporter driven by the germline ε promoter (Pε):

1. HBEGF functions as the receptor for the diphtheria (DT) toxin and confers high sensitivity to DT toxin killing following IL4 induction (for use in survival screening strategies)
2. GFP to monitor IL4 induction of the Pε by fluorescence (FACS)

- The A5T4 screening line consists of the B cell line BJAB engineered to contain the above dual-function HBEGF2a/GFP reporter.

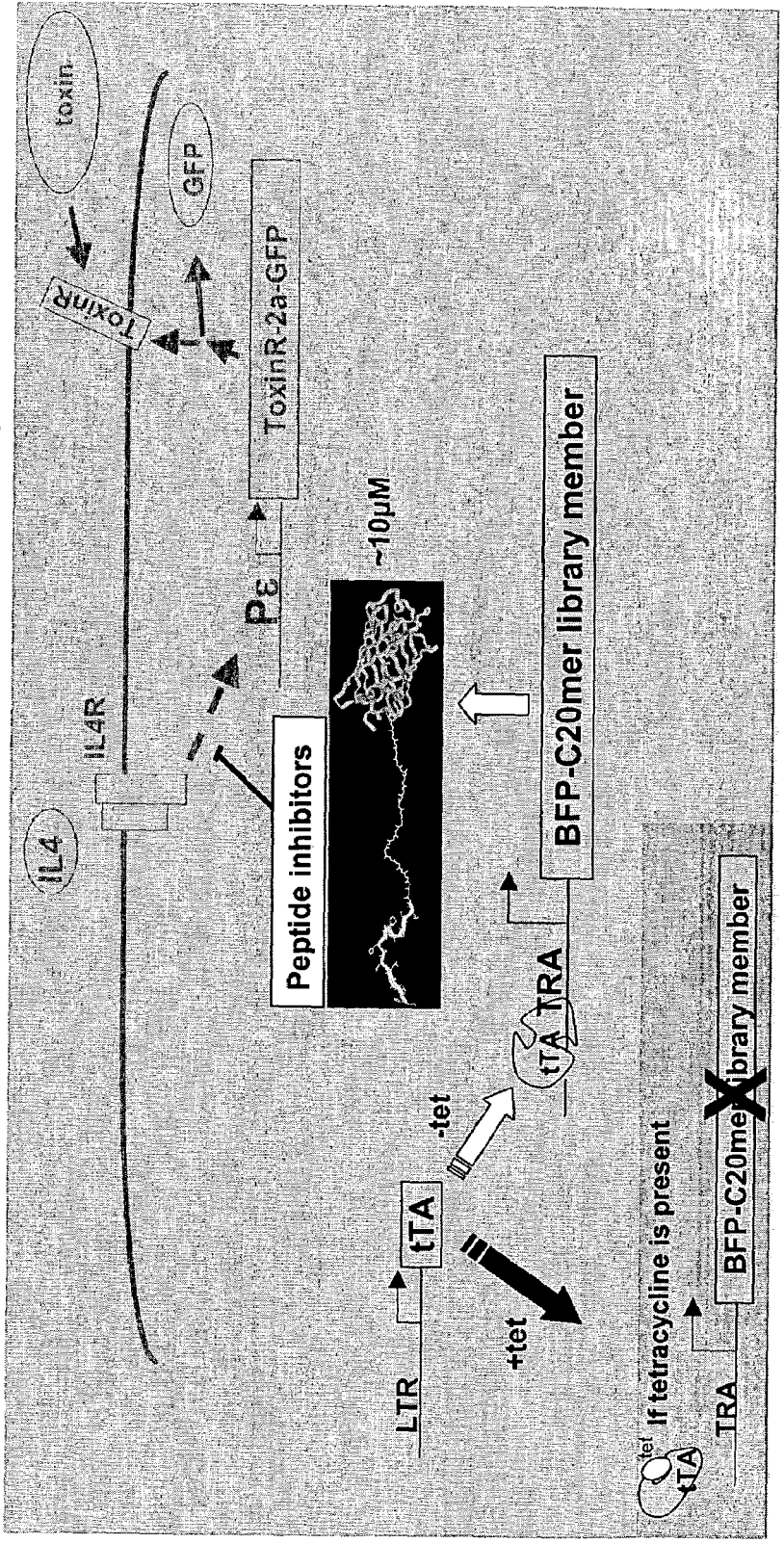

Outline of Enrichment and Screening Procedure

DNA Transfer: DR15wt Peptide Transfers Phenotype

YTH Screening for Potential Targets

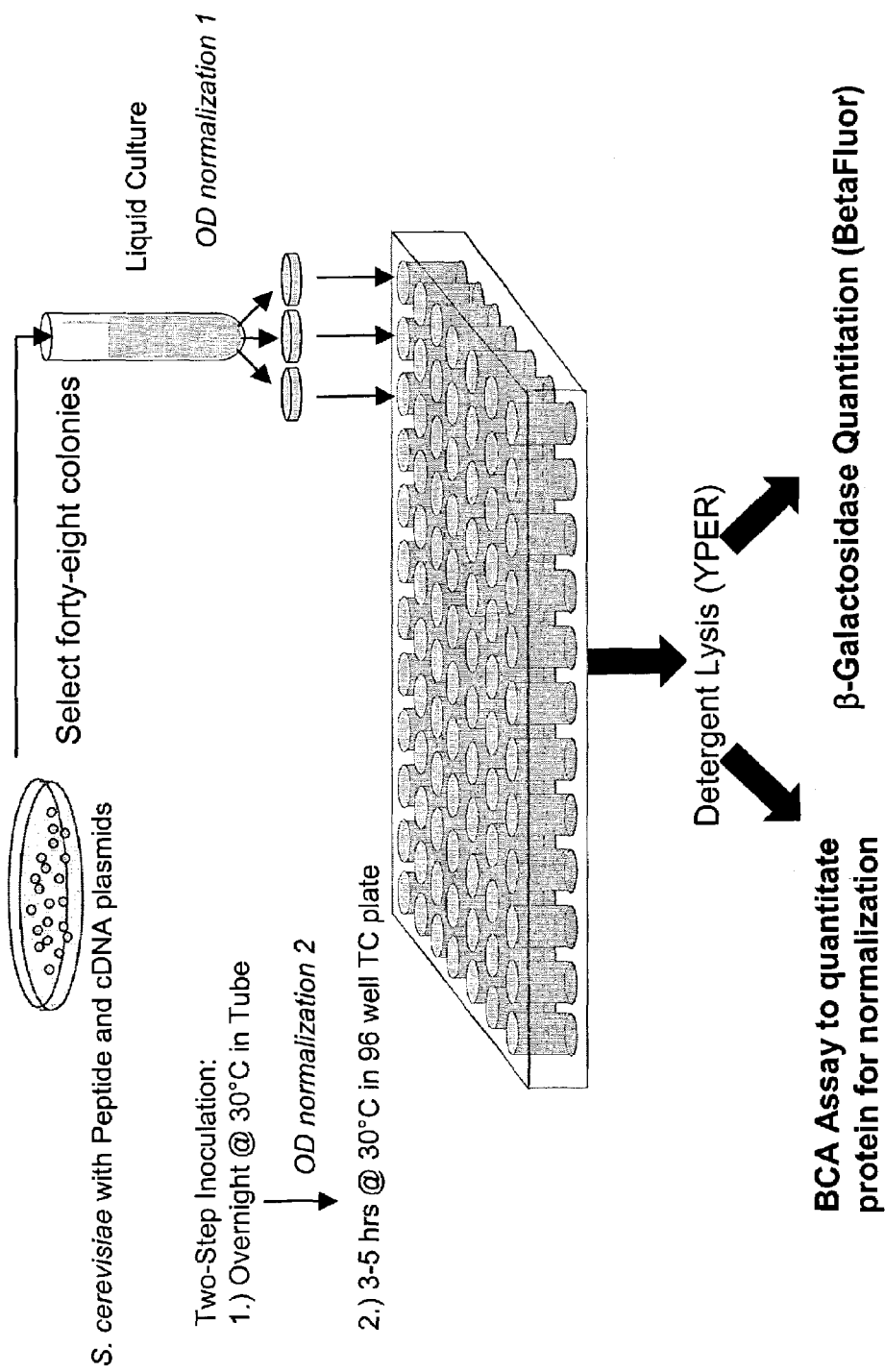

Reconfirmation Strategy

YTH Interaction Profile: DR15wt peptide Binds hTXNL

FIG. 8

Interaction Profile: Selection Criteria

| | A: Reduction of Interaction (ROI) | B: Loss of Interaction (LOI) | C: Increase of Interaction (IOI) | D: Neutral (N) |
|---|---|---|---|---|
| | Statistical reduction (p value) | Statistical reduction (p value) AND greater than 50% reduction | Increase in affinity of 20% OR statistical increase over wild type | Change in affinity less than or equal to 20% OR statistically insignificant change over wild type |
| Restrictions: | | Must not have a B that fails unless countered by 2 other B passes | Must not have an A that fails unless countered by 2 passes of A, B, or C | Must not have both an A and a B that fails |
| Exceptions: | | Can have a C that fails as long as 2 pass A or B and no A or B fail | Can have a D that fails as long as 2 pass A, B, or C | |

Failure is defined as a one-step shift along the linear progression from B to A to D to C; a two-step shift (i.e. from B to D) eliminates a candidate from consideration When more than one YTH cDNA displays a passing mutant profile, hits are ranked by best profile and bioinformatic analysis

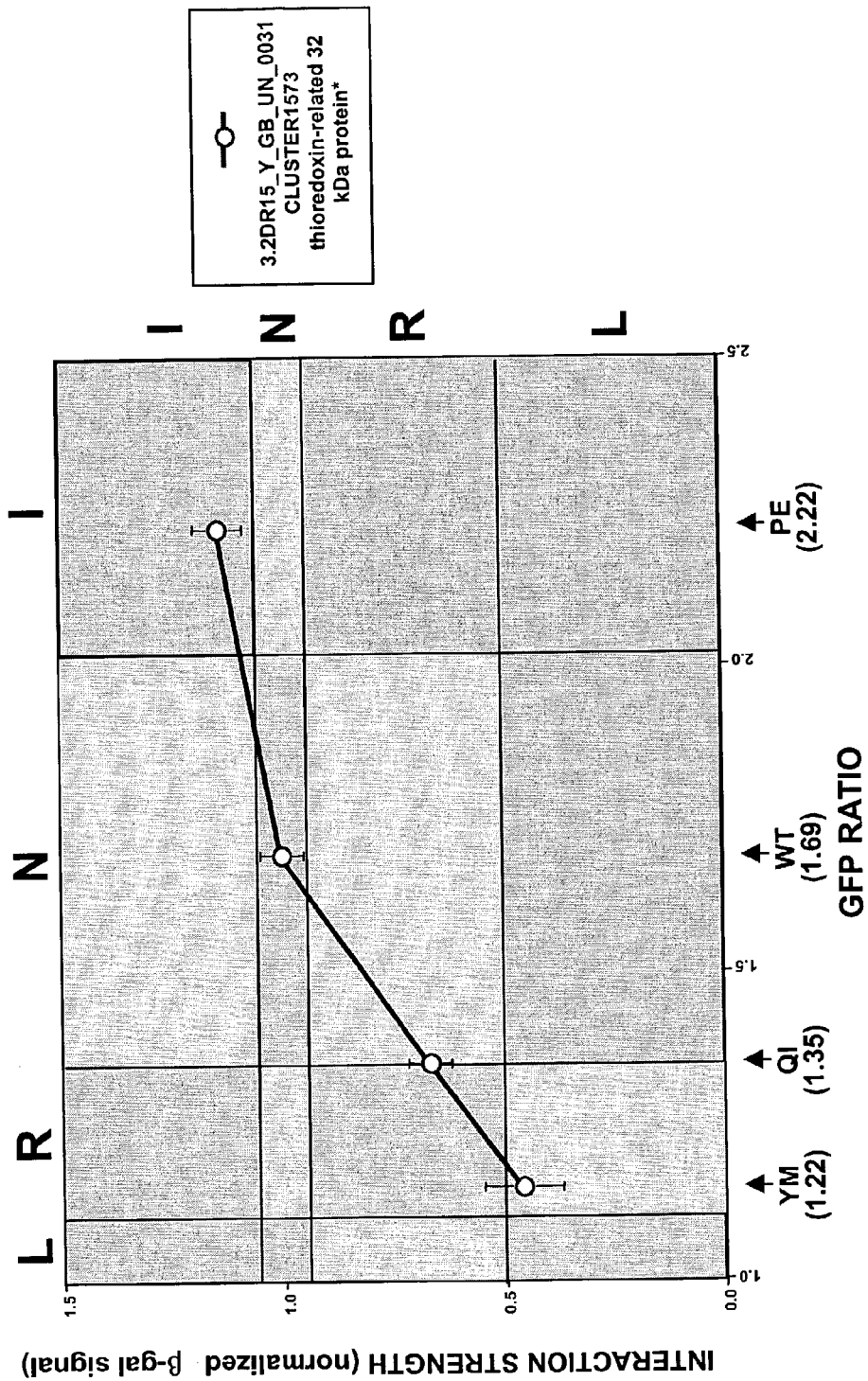

FIG. 10

Amino Acid Sequence of Human TXNL
(SEQ ID NO:5)

```
  1  mvgvkpvgsd pdfqpelsga gsrlavvkft mrgcgpclri apafssmsnk ypqavflevd
 61  vhqcggtaat nnisatptfl ffrnkvridq yggadavgle ekikqhlend pgsnedtdip
121  kgymdlmpfi nkagcecine sdehgfdncl rkdttflesd cdeqllitva fnqpvklysm
181  kfqgpdngqg pkyvkifinl prsmdfeeae rseptqalel teddikedgi vplryvkfqn
241  vnsvtifvqs nqgeeettri syftfigtpv qatnmmdfkr vvgkkgesh
```

METHODS OF IDENTIFYING COMPOUNDS THAT MODULATE IL-4 RECEPTOR-MEDIATED IGE SYNTHESIS UTILIZING A THIOREDOXIN-LIKE 32 KDA PROTEIN

FIELD OF THE INVENTION

The present invention relates to compounds that modulate processes associated with isotype switching of B cells and IgE production, methods and kits for identifying such compounds and methods of using such compounds in a variety of contexts, such as for the treatment or prevention of diseases associated with or characterized by production and/or accumulation of IgE, including anaphylactic hypersensitivity or allergic reactions, allergic rhinitis, allergic conjunctivitis, systemic mastocytosis, hyper IgE syndrome, and IgE gammopathies, atopic disorders such as atopic dermatitis, atopic eczema and atopic asthma, and B-cell lymphoma.

BACKGROUND OF THE INVENTION

The immune system protects the body against invasion by foreign environmental agents such as microorganisms or their products, foods, chemicals, drugs, molds, pollen, animal hair or dander, etc. The ability of the immune system to protect the body against such foreign invaders may be innate or acquired.

The acquired immune response, which stems from exposure to the foreign invader, is extremely complex and involves numerous types of cells that interact with one another in myriad ways to express the full range of immune response. Two of these cell types come from a common lymphoid precursor cell but differentiate along different developmental lines. One line matures in the thymus (T-cells); the other line matures in the bone marrow (B-cells). Although T- and B-cells differ in many functional respects, they share one of the important properties of the immune response: they both exhibit specificity towards a foreign invader (antigen). Thus, the major recognition and reaction functions of the immune response are contained within the lymph cells.

A third cell type that participates in the acquired immune response is the class of cells referred to as antigen-presenting cells (APC). Unlike the T- and B-cells, the APC do not have antigen-specificity. However, they play an important role in processing and presenting the antigen to the T-cells.

While the T- and B-cells are both involved in acquired immunity, they have different functions. Both T- and B-cells have antigen-specific receptors on their surfaces that, when bound by the antigen, activate the cells to release various products. In the case of B-cells, the surface receptors are immunoglobulins and the products released by the activated B-cells are immunoglobulins that have the same specificity for the antigen as the surface receptor immunoglobulins. In the case of activated T-cells, the products released are not the same as their surface receptor immunoglobulins, but are instead other molecules, called cytokines, that affect other cells and participate in the elimination of the antigen. One such cytokine, released by a class of T-cells called helper T-cells, is interleukin-4 (IL-4).

The immunoglobulins produced and released by B-cells must bind to a vast array of foreign invaders (antigens). All immunoglobulins share certain common structural features that enable them to: (1) recognize and bind specifically to a unique structural feature on an antigen (termed an epitope); and (2) perform a common biological function after binding the antigen. Basically, each immunoglobulin consists of two identical light (L) chains and two identical heavy (H) chains. The H chains are linked together via disulfide bridges. The portion of the immunoglobulin that binds the antigen includes the amino-terminal regions of both L and H chains. There are five major classes of H chains, termed $\alpha$, $\delta$, $\epsilon$, $\gamma$ and $\mu$, providing five different isotypes of immunoglobulins: IgA, IgD, IgE, IgG and IgM. Although all five classes of immunoglobulins may possess precisely the same specificity for an antigen, they all have different biological functions.

While the immune system provides tremendous benefits in protecting the body against foreign invaders, particularly those that cause infectious diseases, its effects are sometimes damaging. For example, in the process of eliminating an invading foreign substance some tissue damage may occur, typically as a result of the accumulation of immunoglobulins with non-specific effects. Such damage is generally temporary, ceasing once the foreign invader has been eliminated. However, there are instances, such as in the case of hypersensitivity or allergic reactions, where the immune response directed against even innocuous agents such as inhaled pollen, inhaled mold spores, insect bite products, medications and even foods, is so powerful that it results in severe pathological consequences or symptoms.

Such hypersensitivity or allergic reactions are divided into four classes, designated types I-IV. The symptoms of the type I allergic reactions, called anaphylactic reactions or anaphylaxis, include the common symptoms associated with mild allergies, such as runny nose, watery eyes, etc., as well as the more dangerous, and often fatal, symptoms of difficulty in breathing (asthma), asphyxiation (typically due to constriction of smooth muscle around the bronchi in the lungs) and a sharp drop in blood pressure. Also included within the class of type I allergic reactions are atopic reactions, including atopic dermatitis, atopic eczema and atopic asthma.

Even when not lethal, such anaphylactic allergic reactions produce symptoms that interfere with the enjoyment of normal life. One need only witness the inability of an allergy sufferer to mow the lawn or hike through the woods to understand the disruptive force even mild allergies have on everyday life. Thus, while the immune system is quite beneficial, it would be desirable to be able to interrupt its response to invading foreign agents that pose no risk or threat to the body.

IgE immunoglobulins are crucial immune mediators of such anaphylactic hypersensitivity and allergic reactions, and have been shown to be responsible for the induction and maintenance of anaphylactic allergic symptoms. For example, anti-IgE antibodies have been shown to interfere with IgE function and alleviate allergic symptoms (Jardieu, 1995, Curr. Op. Immunol. 7:779-782; Shields et al., 1995, Int. Arch. Allergy Immunol. 107:308-312). Thus, release and/or accumulation of IgE immunoglobulins are believed to play a crucial role in the anaphylactic allergic response to innocuous foreign invaders. Other diseases associated with or mediated by IgE production and/or accumulation include, but are not limited to, allergic rhinitis, allergic conjunctivitis, systemic mastocytosis, hyper IgE syndrome, IgE gammopathies and B-cell lymphoma.

Although IgEs are produced and released by B-cells, the cells must be activated to do so (B-cells initially produce only IgD and IgM). The isotype switching of B-cells to produce IgE is a complex process that involves the replacement of certain immunoglobulin constant (C) regions with other C regions that have biologically distinct effector functions, without altering the specificity of the immunoglobulin. For IgE switching, a deletional rearrangement of the IgH chain gene locus occurs, which results in the joining of the switch region of the μ gene, Sμ, with the corresponding region of the ε gene, Sε.

This IgE switching is induced in part by IL-4 (or IL-13) produced by T-cells. The IL-4 induction initiates transcription through the Sε region, resulting in the synthesis of germline (or "sterile") ε transcripts (that is, transcripts of the unrearranged Cε H genes) that lead to the production of IgE instead of IgM.

IL-4 induced germline ε transcription and consequent synthesis of IgE is inhibited by interferon gamma (IFN-γ), interferon alpha (IFN-α) and tumor growth factor beta (TGF-β). In addition to the IL-4 signal, a second signal, also normally delivered by T-cells, is required for switch recombination leading to the production of IgE. This second T-cell signal may be replaced by monoclonal antibodies to CD40, infection by Epstein-Barr virus or hydrocortisone.

Generally, traditional treatments for diseases mediated by IgE production and/or accumulation regulate the immune system following synthesis of IgE. For example, traditional therapies for the treatment of allergies include anti-histamines designed to modulate the IgE-mediated response resulting in mast cell degranulation. Drugs are also known that generally downregulate IgE production or that inhibit switching of, but not induction of, germline ε transcription (see, e.g., Loh et al., 1996, J. Allerg. Clin. Immunol. 97(5):1141).

Although these treatments are often effective, treatments that act to reduce or eliminate IgE production altogether would be desirable. By reducing or eliminating IgE production, the hypersensitivity or allergic response may be reduced or eliminated altogether. Accordingly, the availability of compounds that are upstream modulators of IgE production, such as compounds capable of modulating, and in particular inhibiting, IL-4 receptor-mediated germline ε transcription, would be highly desirable.

The ability to screen for compounds capable of modulating IgE production, and in particular compounds that modulate IL-4 (or IL-13) induced germline ε transcription typically involves screening candidate compounds in complex cell-based functional assays, such as the functional assays described in U.S. Pat. No. 5,958,707. These assays typically involve contacting a cell comprising a reporter gene operably linked to a promoter responsive to or inducible by IL-4 with a candidate compound of interest in the presence of IL-4 and assessing the amount of reporter gene product produced. The reporter gene is typically a gene that encodes a protein that produces an observable signal, such as a fluorescent protein. The IL-4 inducible promoter may be a germline ε promoter. Compounds that antagonize (inhibit) IL-4 induced transcription will yield reduced amounts of reporter gene product as compared to control cells contacted with IL-4 alone. Compounds that agonize IL-4 induced transcription will yield increased amounts of reporter gene product as compared to control cells contacted with IL-4 alone. Particularly useful functional assays for screening compounds for the ability to modulate IL-4 inducible germline ε transcription are described in U.S. Pat. No. 5,958,707, WO 99/58663 and WO 01/34806.

Although such functional screening assays are quite powerful and effective, simpler assays that could be performed in cell-free systems and/or that do not require a functional component, such as simple binding assays with isolated proteins known to be involved in the IL-4 signaling cascade responsible for the production of germline ε transcripts, and hence the production of IgE, would be beneficial.

SUMMARY OF THE INVENTION

These and other objects are furnished by the present invention, which in one aspect provides compounds, referred to herein as DR15 compounds, which are capable of modulating, and in particular inhibiting, the IL-4 receptor-mediated signaling cascade involved in B-cell isotype switching to, and consequent production of, IgE. The DR15 compounds of the invention are generally 8 to 30 amino acid residue peptides or peptide analogs, or pharmaceutically-acceptable salts thereof, characterized by structural formula (I):

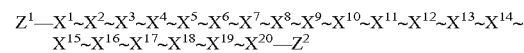

wherein:
$X^1$ is a small aliphatic or a conformationally constrained residue;
$X^2$ is a small aliphatic or an acidic residue;
$X^3$ is a basic residue;
$X^4$ is a polar hydrophilic residue;
$X^5$ is a small aliphatic or an aromatic residue;
$X^6$ is a small aliphatic or a non-polar residue;
$X^7$ is a basic residue;
$X^8$ is a non-polar residue;
$X^9$ is a conformationally constrained residue;
$X^{10}$ is a conformationally constrained residue;
$X^{11}$ is a polar residue;
$X^{12}$ is a small polar residue;
$X^{13}$ is an aliphatic residue;
$X^{14}$ is a small aliphatic residue;
$X^{15}$ is an acidic residue;
$X^{16}$ is a small aliphatic residue;
$X^{17}$ is a polar or a small aliphatic residue;
$X^{18}$ is an aliphatic residue;
$X^{19}$ is an aromatic residue;
$X^{20}$ is a small polar residue;
$Z^1$ is RRN—, RC(O)NR—, RS(O)$_2$NR— or an amino-terminal blocking group;
$Z^2$ is —C(O)OR, —C(O)O—, —C(O)NRR or a carboxyl-terminal blocking group;
each R is independently selected from the group consisting of hydrogen, alkyl, substituted alkyl, aryl, substituted aryl, arylalkyl, substituted arylalkyl, heteroaryl, substituted heteroaryl, heteroarylalkyl and substituted heteroarylalkyl;
each "~" independently represents an amide, a substituted amide or an isostere of an amide;
each "—" represents a bond, or a 1 to 10 residue peptide or peptide analog; and
wherein one or more of $X^1$, $X^2$, $X^{19}$, or $X^{20}$ may be absent.

The DR15 compounds of the invention preferably have between 10 and 25 residues; more preferably, the DR15 compounds of the invention have between 12 and 20 residues. In particular, the more preferred embodiments have 12, 13, 14, 15, 16, 17, 18, 19 or 20 residues.

Particular DR15 compounds of the invention include

```
DR15wt  (PERCYMRMPPQSLADAQIYS),    (SEQ ID NO:1)
DR15PE  (AARCYMRMPPQSLADAQIYS),    (SEQ ID NO:2)
```

-continued

DR15QI (PERCYMRMPPQSLADAAAYS), (SEQ ID NO:3)

DR15YM (PERCAARMPPQSLADAQIYS). (SEQ ID NO:4)

The DR15 compounds of the invention inhibit IL-4 (or IL-13) induced germline ε transcription in cellular assays. As a consequence of this activity, the DR15 compounds of the invention can be used to modulate the IL-4 receptor-mediated signaling cascade involved in isotype switching to, and consequent production of, IgE. In a specific embodiment, the DR15 compounds may be used to inhibit IL-4 (or IL-13) induced IgE production as a therapeutic approach towards the treatment or prevention of diseases associated with, characterized by or caused by IgE production and/or accumulation, such as anaphylactic hypersensitivity or allergic reactions and/or symptoms associated with such reactions, allergic rhinitis, allergic conjunctivitis, systemic mastocytosis, hyper IgE syndrome, IgE gammopathies, atopic disorders such as atopic dermatitis, atopic eczema and/or atopic asthma, and B-cell lymphoma. The DR15 compounds of the invention can also be used in assays to identify other compounds capable of effecting the above activities, as will be described in more detail, below.

In addition to their ability to inhibit IL-4 (or IL-13) inducible germline ε transcription, and hence IL-4 receptor-mediated IgE production, the DR15 compound of the invention also bind thioredoxin-like 32 kDa proteins (TXNL). In particular, three DR15 compounds of the invention, DR15wt (PERCYMRMPPQSLADAQIYS; SEQ ID NO:1), peptide DR15PE (AARCYMRMPPQSLADAQIYS; SEQ ID NO:2), peptide DR15QI (PERCYMRMPPQSLADAAAYS; SEQ ID NO:3) and peptide DR15YM (PERCAARMPPQSLADAQIYS; SEQ ID NO: 4) were found to bind human thioredoxin-like 32 kDa protein (hTXNL) (NCBI Sequence Database #NP_004777 (SEQ ID NO:5), corresponding nucleotide sequence at NCBI #NM_004786) in a yeast two hybrid interaction assay. Quite significantly, the ability of these DR15 compounds to bind the hTXNL in this assay correlates with their observed ability to inhibit IL-4 (or IL-13) induced germline ε transcription. These observations provide the first evidence directly linking TXNL to the IL-4 receptor-mediated signaling cascade responsible for isotype switching to, and consequent production of, IgE, and in particular as being an effector of germline ε transcription. Hence, these observations provide the first evidence directly linking TXNL to the upstream regulation of isotype switching and/or IgE production.

This significant discovery enables the ability to use a TXNL as a "surrogate" analyte in screening assays to identify compounds that modulate or regulate the IL-4 receptor-mediated signaling cascade leading to the production of IgE. Since induction of the ε promoter in response to IL-4 (or IL-13) is the first recognizable step necessary for isotype switching and consequent production of IgE, inhibition of IL-4 (or IL-13) induced transcription of the ε promoter should prevent B-cells from switching to and/or producing IgE. This significant discovery therefore permits the ability to use a TXNL as a surrogate analyte in simple binding assays to identify compounds having a variety of in vitro, in vivo and ex vivo therapeutic uses.

Accordingly, in another aspect, the invention provides methods of identifying compounds that modulate, and in particular inhibit, the IL-4 receptor-mediated signaling cascade leading to the production of IgE. The methods generally comprise determining whether a candidate compound of interest binds a TXNL, wherein the ability to bind the TXNL identifies the compound as being a modulator of the IL-4 receptor-mediated signaling cascade leading to the production of IgE. In one embodiment of the method, it is determined whether the candidate compound competes for binding to the TXNL with a DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4). In a specific embodiment of the method, compounds that inhibit IL-4 (or IL-13) induced germline ε transcription are identified. In a further embodiment, the methods comprise determining whether a candidate compound of interest is a TXNL antagonist. The determination of the candidate compound as a TXNL antagonist can be made in addition to, or as an alternative to, the determination of the ability of the candidate compound to bind to a DR15 compound.

In yet another aspect, the invention provides methods of identifying compounds that inhibit isotype switching of B-cells to produce IgE and/or IgE production. The methods generally comprise determining whether a candidate compound of interest binds a TXNL, wherein the ability to bind the TXNL identifies the compound as being an inhibitor of isotype switching and/or IgE production. In one embodiment of the method, it is determined whether the candidate compound competes for binding to the TXNL with a DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4). In a specific embodiment of the method, compounds that inhibit IgE production are identified. In another specific embodiment, compounds that inhibit IL-4 receptor-mediated IgE production are identified. In still another specific embodiment, compounds that inhibit TXNL-mediated IgE production are identified.

In still another aspect, the invention provides methods of identifying compounds that modulate, and in particular inhibit or downregulate, processes mediated by or associated with IL-4 receptor-mediated B-cell isotype switching and/or IgE production and/or accumulation. Such processes include, but are not limited to, anaphylactic hypersensitivity or allergic reactions and/or symptoms associated with such reactions, allergic rhinitis, allergic conjunctivitis, systemic mastocytosis, hyper IgE syndrome, and IgE gammopathies, atopic disorders such as atopic dermatitis, atopic eczema and/or atopic asthma, and B-cell lymphoma. The methods generally involve determining whether a candidate compound of interest binds a TXNL, where the ability to bind the TXNL identifies the compound as being a modulator of a process mediated by or associated with IL-4 receptor-mediated isotype switching and/or IgE production and/or accumulation. In one embodiment of the method, it is determined whether the candidate compound competes for binding the TXNL with a DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4).

In yet another aspect, the invention provides methods of identifying compounds useful for treating disorders associated with, or mediated or caused by, IgE production and/or accumulation. The methods generally comprise determining whether a candidate compound of interest binds an TXNL, wherein the ability to bind the TXNL identifies the compound as being useful for treating disorders associated with, or mediated or caused by, IgE production and/or accumulation. In one embodiment of the method, it is determined whether the candidate compound competes for binding the TXNL with a DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4). Diseases associated with, or mediated or caused by, IgE production and/or accumulation for which therapeutic compounds may be identified according to the methods include, but are not limited to, anaphylactic hypersensitivity or allergic reactions and/or symptoms associated with such reactions, allergic rhinitis, allergic conjunctivitis, systemic mastocytosis, hyper IgE syndrome, and IgE gammopathies, atopic disorders such as atopic dermatitis, atopic eczema and atopic asthma, and B-cell lymphoma.

In another aspect, the invention provides compounds identified by the various screening methods of the invention.

In still another aspect, the invention provides pharmaceutical compositions. The compositions generally comprise a DR15 compound of the invention, a compound that competes for binding a TXNL with a DR15 compound of the invention or a compound identified by the screening methods of the invention and a pharmaceutically-acceptable carrier, excipient or diluent.

In yet another aspect, the invention provides methods of modulating, and in particular inhibiting or downregulating, the IL-4 receptor-mediated signaling cascade involved in B-cell isotype switching to produce, and/or consequent production of, IgE, or processes involved in this signal transduction cascade, such as IL-4 (or IL-13) induced germline ε transcription. The method generally involves administering to a cell a compound that binds a TXNL in an amount effective to modulate this IL-4 receptor-mediated signaling cascade. In one embodiment of the method, the compound inhibits IL-4 (or IL-13) induced germline ε transcription. In another specific embodiment, the compound inhibits TXNL-mediated germline ε transcription. The method may be practiced in vitro, in vivo or ex vivo. In one embodiment, the cell is administered a DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4), or a compound that competes for binding to a TXNL with an active DR15 compound of the invention.

In yet another aspect, the invention provides methods of modulating, and in particular inhibiting or downregulating, isotype switching to IgE and/or IgE production. The method generally involves administering to a cell an amount of a compound that binds an TXNL effective to modulate isotype switching to IgE and/or IgE production. The method may be practiced in vitro, in vivo or ex vivo. In one embodiment, the cell is administered a DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4), or a compound that competes for binding to a TXNL with an active DR15 compound of the invention.

In still another aspect, the invention provides methods of treating or preventing diseases associated with, or mediated or caused by, IgE production and/or accumulation. The method generally comprises administering to an animal suffering from such a disease an amount of a compound that binds a TXNL effective to treat or prevent the disease and/or one or more of its symptoms. In one embodiment, the compound administered is a DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4). In another embodiment, the compound administered is a compound that competes for binding to a TXNL with an active DR15 compound of the invention. Diseases associated with, or mediated or caused by, IgE production and/or accumulation that may be treated or prevented according to the methods of the invention include, but are not limited to, anaphylactic hypersensitivity or allergic reactions (including food and drug allergies), and/or symptoms associated with such reactions, allergic rhinitis, allergic conjunctivitis, systemic mastocytosis, hyper IgE syndrome, IgE gammopathies, atopic disorders such as atopic dermatitis, atopic eczema and/or atopic asthma, and B-cell lymphoma. The method may be practiced therapeutically to treat the disease once the onset of the disease and/or its associated symptoms have already occurred, or prophylactically to prevent the onset of the disease and/or its associated symptoms. The methods may be practiced in veterinary contexts or in the treatment of humans.

In a final aspect, the invention provides kits for carrying out the various methods of the invention. In one embodiment, the kit comprises a TXNL and a DR15 compound of the invention or a compound that competes for binding the TXNL with a DR15 compound of the invention. The kit may further include additional components for carrying out the methods of the invention, such as, by way of example and not limitation, buffers, labels and/or labeling reagents and/or instructions teaching methods of using the kits.

BRIEF DESCRIPTION OF THE FIGURES

FIG. 1 illustrates the nucleotide sequence of a 603 bp fragment of the human germline ε promoter (SEQ ID NO:6);

FIG. 2A provides a cartoon illustrating the diphtheria toxin (DT) selection of reporter cell line A5T4;

FIG. 2B provides a cartoon illustrating the tetracycline/doxycycline controlled peptide expression system of reporter cell line A5T4;

FIG. 5B provides a cartoon illustrating a yeast two hybrid (YTH) assay used to identify hTXNL as a binding partner or target for peptide DR15wt;

FIG. 6 provides a cartoon summarizing strategies for reconfirming potential targets identified in the YTH assay depicted in FIG. 5A;

FIG. 7 provides interaction graphic profiles for peptide DR15wt and mutants derived therefrom;

FIG. 8 provides selection criteria for the interaction profiling method used to confirm hTXNL as a binding partner for peptide DR15wt;

FIG. 9 provides weighted graphic interaction/functional profiles for peptide DR15wt and mutants derived therefrom;

FIG. 10 illustrates the amino acid sequence for human TXNL (SEQ ID NO: 5).

DETAILED DESCRIPTION OF THE PREFERRED EMBODIMENTS

Abbreviations

The abbreviations used for the genetically encoded amino acids are conventional and are as follows:

Figure 3:
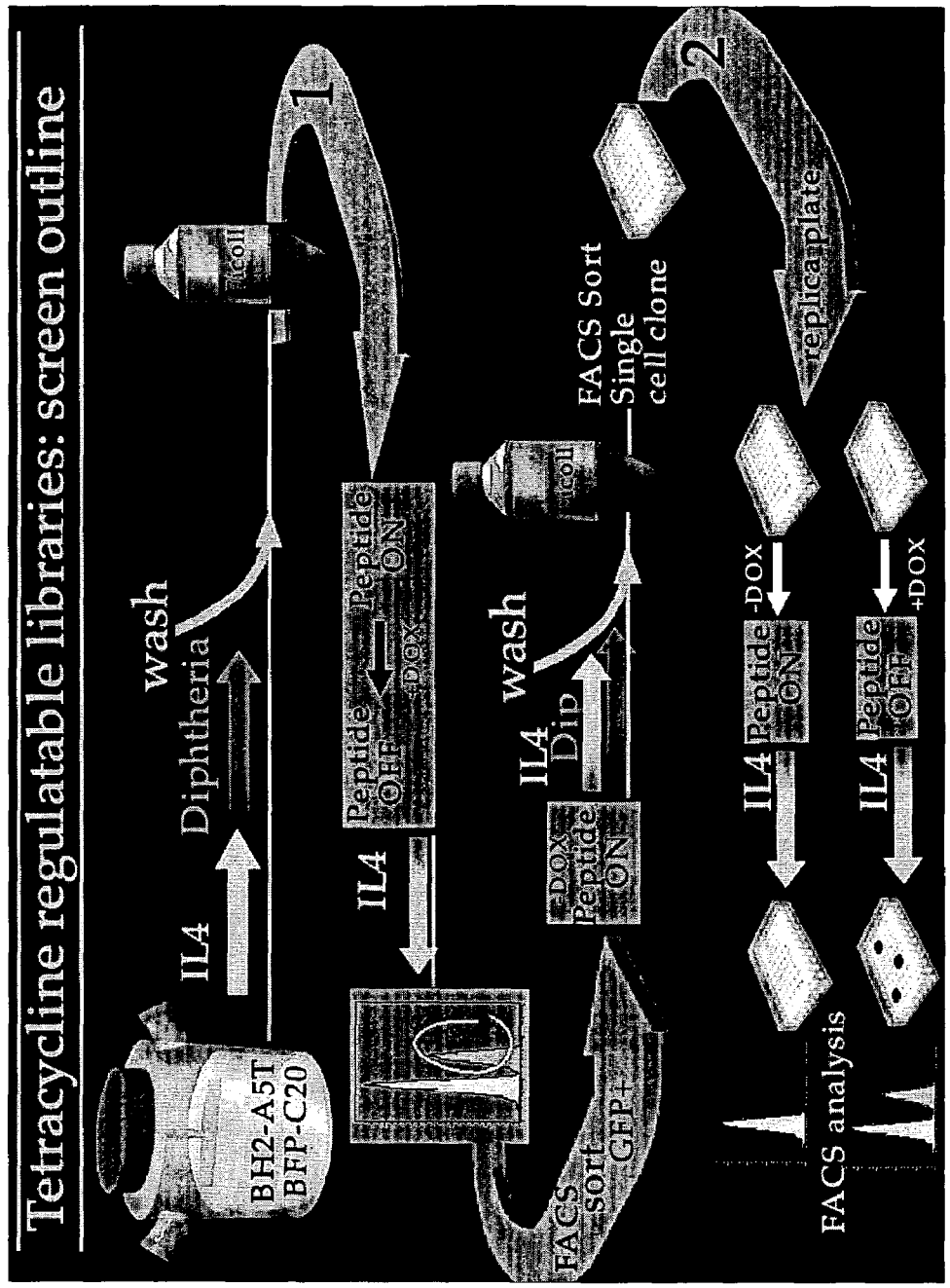
FIG. 3 provides a cartoon illustrating the enrichment and screening procedure used to identify certain DR15 compounds of the invention.

| Amino Acid | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D," the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the N→C direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleotides may be either ribonucleosides or 2'-deoxyribonucleosides. The nucleosides may be specified as being either ribonucleosides or 2'-deoxyribonucleosides on an individual basis or on an aggregate basis. When specified on an individual basis, the one-letter abbreviation is preceded by either a "d" or an "r," where "d" indicates the nucleoside is a 2'-deoxyribonucleoside and "r" indicates the nucleoside is a ribonucleoside. For example, "dA" designates 2'-deoxyriboadenosine and "rA" designates riboadenosine. When specified on an aggregate basis, the particular nucleic acid or polynucleotide is identified as being either an RNA molecule or a DNA molecule. Nucleotides are abbreviated by adding a "p" to represent each phosphate, as well as whether the phosphates are attached to the 3'-position or the 5'-position of the sugar. Thus, 5'-nucleotides are abbreviated as "pN" and 3'-nucleotides are abbreviated as "Np," where "N" represents A, G, C, T or U. When nucleic acid sequences are presented as a string of one-letter abbreviations, the sequences are presented in the 5'→3' direction in accordance with common convention, and the phosphates are not indicated.

Definitions

As used throughout the instant application, the following terms shall have the following meanings:

"Promoter" or "Promoter Sequence" refers to a DNA regulatory region capable of initiating transcription of a downstream (3' direction) coding sequence. A promoter typically includes a transcription initiation site (conveniently defined, for example, by mapping with nuclease S1) and protein binding domains responsible for binding proteins that initiate transcription.

"TGF-β Inducible Promoter" refers to a promoter that initiates transcription when a cell comprising a nucleic acid molecule including such a promoter is exposed to, or contacted with, TGF-β. While not intending to be bound by any particular theory of operation, it is believed that contacting a cell comprising such a promoter with TGF-β causes the activation of a DNA-binding protein that then binds the TGF-β inducible promoter and induces transcription of coding sequences downstream of the promoter An "α promoter" or a "germline α promoter" is a TGF-β inducible promoter that, when induced in a B-cell, leads to the production of IgA immunoglobulins. Such germline α promoters are well-known in the art. Such promoters may be endogenous to a cell, or alternatively, they may be engineered or exogenously supplied.

"IL-4 inducible promoter" refers to a promoter that initiates transcription when a cell comprising a nucleic acid molecule including such a promoter is exposed to, or contacted with, IL-4 or IL-13. While not intending to be bound by any particular theory of operation, it is believed that contacting a cell comprising such a promoter with IL-4 (or IL-13) causes the activation of a DNA-binding protein that then binds the IL-4 inducible promoter and induces transcription of coding sequences downstream of the promoter.

An "ε promoter" or a "germline ε promoter" is an IL-4 inducible promoter that, when induced in a B-cell, leads to the production of IgE immunoglobulins. Such IL-4 inducible germline ε promoters are well-known in the art. Such promoters may be endogenous to a cell or, alternatively, they may be engineered or supplied exogenously. A specific example of a germline ε promoter is the 603 bp IL-4 inducible fragment of the human ε promoter depicted in FIG. 1 (SEQ ID NO:6).

A compound that "modulates an IL-4 inducible germline ε promoter" or that "modulates IL-4 induced germline ε transcription" has the ability to change or alter expression downstream of the germline ε promoter induced by IL-4 (or IL-13). The change in IL-4 induced downstream expression may occur at the mRNA (transcriptional) level or at the protein (translational) level. Hence, the change in IL-4 induced downstream expression may be monitored at the RNA level, for example by quantifying induced downstream transcription products, or at the protein level, for example by quantifying the amount or activity of induced downstream translation products. The compound may act to modulate the IL-4 inducible germline ε promoter via any mechanism of action. For example, the compound may act to modulate the IL-4 inducible germline ε promoter by interacting with or binding a DNA binding protein involved in the IL-4 induced transcription, or by interacting with or binding the IL-4 inducible germline ε promoter per se, or by interacting with or binding to a molecule that functions in the signalling cascade triggered by IL-4.

A compound that "modulates IL-4 receptor-mediated IgE production and/or accumulation" has the ability to change or alter the amount of IgE produced and/or accumulated by a B-cell activated via the IL-4 receptor with IL-4 (or IL-13 or other IL-4 receptor ligand) and, in some cases, a second signal known to cause, in combination with IL-4 (or IL-13), isotype switching of B-cells to produce IgE. Such second signal may be, for example, anti-CD40 monoclonal antibodies (anti-CD40 mAbs), infection by Epstein-Barr virus or hydrocortisone. The compound may act to modulate IL-4 receptor-mediated IgE production and/or accumulation by any mechanism of action. For example, the compound may act to modulate IL-4 induced germline ε transcription, and hence isotype switching, or the compound may act to modulate IgE production and/or accumulation in an already switched cell. An "IL-4 induced" activity includes activity (e.g., production of IgE, transcription of germline ε promoter isotype switching of B-cell) that is induced as a result of the binding of IL-4, IL-13 or other IL-4 receptor ligand to the IL-4 receptor.

"Identifying" in the context of screening assays means determining whether a candidate compound unknown to possess a particular property of interest possesses the property of interest, as well as confirming that a compound thought or known to possess a particular property of interest possesses the property of interest.

Compounds that "compete for binding with a DR15 compound" compete for binding to an TXNL (defined in a later section) with an active DR15 compound of invention (described in more detail in a later section), such as peptide DR15wt (SEQ ID NO:1), peptide DR15PE (SEQ ID NO:2), peptide DR15QI (SEQ ID NO:3), or peptide DR15YM (SEQ ID NO:4), or with another compound that competes for binding to an TXNL with an active DR15 compound of the invention. For example, if compound 1 competes for binding to an TXNL with an active DR15 compound and a candidate compound competes for binding to the TXNL with compound 1, then for purposes of the present invention, the candidate compound competes for binding with a DR15 compound. Where competition with a specific category of compound is intended, the modifiers "directly" and "indirectly" are used, where "directly" refers to competition with the stated compound and "indirectly" refers to competition with another compound that itself competes with the stated compound.

"Alkyl" by itself or as part of another substituent refers to a saturated or unsaturated, branched, straight-chain or cyclic monovalent hydrocarbon group having the stated number of carbon atoms (i.e., $C_1$-$C_6$ means from one to six carbon atoms) derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups composed of from 1 to 6 carbon atoms.

"Alkanyl" by itself or as part of another substituent refers to a saturated branched, straight-chain or cyclic alkyl group.

Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Aryl" by itself or as part of another substituent refers to a monovalent aromatic hydrocarbon group having the stated number of carbon ring atoms (i.e., $C_5$-$C_{14}$ means from 5 to 14 carbon ring atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is ($C_5$-$C_{14}$) aryl, with ($C_5$-$C_{10}$) being even more preferred. Particularly preferred aryls are cyclopentadienyl, phenyl and naphthyl.

"Arylalkyl" by itself or as part of another substituent refers to an acyclic alkyl group in which one of the hydrogen atoms bonded to a carbon atom, typically a terminal or sp³ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In preferred embodiments, the arylalkyl group is ($C_6$-$C_{16}$) arylalkyl, e.g., the alkanyl, alkenyl or alkynyl moiety of the arylalkyl group is ($C_1$-$C_6$) and the aryl moiety is ($C_5$-$C_{10}$). In particularly preferred embodiments the arylalkyl group is ($C_6$-$C_{13}$), e.g., the alkanyl, alkenyl or alkynyl moiety of the arylalkyl group is ($C_1$-$C_3$) and the aryl moiety is ($C_5$-$C_{10}$).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Also included in the definition of "parent heteroaromatic ring system" are those recognized rings that include substituents, such as benzopyrone. Typical parent heteroaromatic ring systems include, but are not limited to, arsindole, benzodioxan, benzofuran, benzopyrone, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (i.e., "5-14 membered" means from 5 to 14 ring atoms) derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5-14 membered heteroaryl, with 5-10 membered heteroaryl being particularly preferred.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In particularly preferred embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

"Substituted Alkyl, Aryl, Arylalkyl, Heteroaryl or Heteroarylakyl" refers to an alkyl, aryl, arylalkyl, heteroaryl or heteroarylakyl group in which one or more hydrogen atoms is replaced with another substituent group. Exemplary substituent groups include, but are not limited to, —OR', —SR', —NR'R', —NO$_2$, —NO, —CN, —CF$_3$, halogen (e.g., —F, —Cl, —Br and —I), —C(O)R', —C(O)OR', —C(O)NR', —S(O)$_2$R', —S(O)$_2$NR'R', where each R' is independently selected from the group consisting of hydrogen and ($C_1$-$C_6$) alkyl.

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

While all of the above mentioned algorithms and programs are suitable for a determination of sequence alignment and % sequence identity, for determination of % sequence identity in connection with the present invention, the BESTFIT or GAP programs in the GCG Wisconsin Software package (Accelrys, Madison Wis.),using default parameters provided, are preferred.

The DR15 Compounds

The DR15 compounds of the invention are generally peptides and/or peptides analogs which, as will be discussed in more detail below, are capable of modulating a variety of processes involved in IL-4 receptor-mediated isotype switching of B-cells to produce IgE. The DR15 compounds of the invention are generally peptides or peptide analogs, or pharmaceutically-acceptable salts thereof, that are from 8 to 30 residues in length and include a "core" peptide or peptide analog, comprising at least 8 consecutive amino acid residues, preferably at least 10 consecutive amino acid residues, more preferably at least 12 amino acid residues, according to structural formula (II):

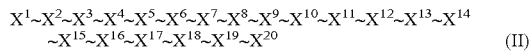

(II)

wherein:

$X^1$ is a small aliphatic or a conformationally constrained residue;

$X^2$ is a small aliphatic or an acidic residue;

$X^3$ is a basic residue;

$X^4$ is a polar hydrophilic residue;

$X^5$ is a small aliphatic or an aromatic residue;

$X^6$ is a small aliphatic or a non-polar residue;

$X^7$ is a basic residue;

$X^8$ is a non-polar residue;

$X^9$ is a conformationally constrained residue;

$X^{10}$ is a conformationally constrained residue;

$X^{11}$ is a polar residue;

$X^{12}$ is a small polar residue;

$X^{13}$ is an aliphatic residue;

$X^{14}$ is a small aliphatic residue;

$X^{15}$ is an acidic residue;

$X^{16}$ is a small aliphatic residue;

$X^{17}$ is a polar or a small aliphatic residue;

$X^{18}$ is an aliphatic residue;

$X^{19}$ is an aromatic residue;

$X^{20}$ is a small polar residue;

The DR15 compounds of the invention include linear, branched and cyclic peptides and peptide analogs.

The DR15 compounds of the invention and/or the "core" peptides or peptide analogs of structure (II) are defined, in part, in terms of amino acids or residues bearing side chains belonging to certain designated classes. The definitions of the various classes of amino acids or residues that define structure (II), and hence the DR15 compounds of the invention, are as follows:

"Hydrophilic Amino Acid or Residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic Amino Acid or Residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic Amino Acid or Residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-His (H), L-Arg (R) and L-Lys (K).

"Polar Amino Acid or Residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic Amino Acid or Residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic Amino Acid or Residue" refers to a hydrophilic or hydrophobic amino acid or residue having a side chain that includes at least one aromatic or heteroaromatic ring. The aromatic or heteroaromatic ring may contain one or more substituents such as —OH, —OR", —SH, —SR", —CN, halogen (e.g., —F, —Cl, —Br, —I), —NO$_2$, —NO, —NH$_2$, —NHR", —NR"R", —C(O)R", —C(O)O$^-$, —C(O)OH, —C(O)OR", —C(O)NH$_2$, —C(O)NHR", —C(O)NR"R" and the like, where each R" is independently (C$_1$-C$_6$) alkyl, substituted (C$_1$-C$_6$) alkyl, (C$_2$-C$_6$) alkenyl, substituted (C$_2$-C$_6$) alkenyl, (C$_2$-C$_6$) alkynyl, substituted (C$_2$-C$_6$) alkynyl, (C$_5$-C$_{10}$) aryl, substituted (C$_5$-C$_{10}$) aryl, (C$_6$-C$_{16}$) arylalkyl, substituted (C$_6$-C$_{16}$) arylalkyl, 5-10 membered heteroaryl, substituted 5-10 membered heteroaryl, 6-16 membered heteroarylalkyl or substituted 6-16 membered heteroarylalkyl. Genetically encoded aromatic amino acids include L-Phe (F), L-Tyr (Y) and L-Trp (W). Although owing to the pKa of its heteroaromatic nitrogen atom L-His (H) is classified above as a basic residue, as its side chain includes a heteroaromatic ring, it may also be classified as an aromatic residue.

"Non-polar Amino Acid or Residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Leu (L), L-Val (V), L-Ile (I), L-Met (M) and L-Ala (A).

"Aliphatic Amino Acid or Residue" refers to a hydrophobic amino acid or residue having an aliphatic hydrocarbon side chain. Genetically encoded aliphatic amino acids include L-Ala (A), L-Val (V), L-Leu (L) and L-Ile (I).

The amino acid L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present invention L-Cys (C) is categorized as a polar hydrophilic amino acid, notwithstanding the general classifications defined above.

The amino acid Gly (G) is also unusual in that it bears no side chain on its α-carbon and, as a consequence, contributes only a peptide bond to a particular peptide sequence. Moreover, owing to the lack of a side chain, it is the only genetically-encoded amino acid having an achiral α-carbon. Although Gly (G) exhibits a hydrophobicity of 0.48 according to the normalized consensus scale of Eisenberg (Eisenberg et al., 1984, supra), for purposes of the present invention, Gly is categorized as an aliphatic amino acid or residue.

Owing in part to its conformationally constrained nature, the amino acid L-Pro (P) is also unusual. Although it is categorized herein as a hydrophobic amino acid or residue, it will typically occur in positions near the N- and/or C-termini so as not to deleteriously affect the structure of the DR15 compounds. However, as will be appreciated by skilled artisans, DR15 compounds may include L-Pro (P) or other similar "conformationally constrained" residues at internal positions.

"Small Amino Acid or Residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include Gly, L-Ala (A), L-Val (V), L-Cys (C), L-Asn (N), L-Ser (S), L-Thr (T) and L-Asp (D).

"Hydroxyl-containing residue" refers to an amino acid containing a hydroxyl (—OH) moiety. Genetically-encoded hydroxyl-containing amino acids include L-Ser (S) L-Thr (T) and L-Tyr (Y).

As will be appreciated by those of skill in the art, the above-defined categories are not mutually exclusive. Indeed, the delineated category of small amino acids includes amino acids from all of the other delineated categories except the aromatic category. Thus, amino acids having side chains exhibiting two or more physico-chemical properties can be included in multiple categories. As a specific example, amino acid side chains having heteroaromatic moieties that include ionizable heteroatoms, such as His, may exhibit both aromatic properties and basic properties, and can therefore be included in both the aromatic and basic categories. The appropriate classification of any amino acid or residue will be apparent to those of skill in the art, especially in light of the detailed disclosure provided herein.

While the above-defined categories have been exemplified in terms of the genetically encoded amino acids, the DR15 compounds of the invention are not restricted to the genetically encoded amino acids. Indeed, in addition to the genetically-encoded amino acids, the DR15 compounds of the invention may be comprised, either in whole or in part, of naturally-occurring and/or synthetic non-encoded amino acids. Certain commonly encountered non-encoded amino acids of which the cyclic compounds of the invention may be comprised include, but are not limited to: the D-enantiomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the compounds of the invention may be comprised will be apparent to those of skill in the art (see, e.g., the various amino acids provided in Fasman, 1989, *CRC Practical Handbook of Biochemistry and Molecular Biology*, CRC Press, Boca Raton, Fla., at pp. 3-70 and the references cited therein, all of which are incorporated by reference). These amino acids may be in either the L- or D-configuration.

Those of skill in the art will recognize that amino acids or residues bearing side chain protecting groups may also comprise the DR15 compounds of the invention. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His(benzyl), His(tos), Lys(fmoc), Lys(tos), Ser(O-benzyl), Thr(O-benzyl) and Tyr(O-benzyl).

Non-encoding amino acids that are conformationally constrained of which the DR15 compounds of the invention may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

The classifications of the genetically encoded and certain common non-encoded amino acids according to the categories defined above are summarized in TABLE 1, below. It is to be understood that TABLE 1 is for illustrative purposes only and does not purport to be an exhaustive list of amino acids that can comprise the DR15 compounds of the invention. Other amino acids not specifically mentioned herein can be readily categorized based on their observed physical and chemical properties in light of the definitions provided herein.

TABLE 1

Encoded and Certain Common Non-Encoded Amino Acid Classifications

| Classification | Encoded Amino Acids | Non-encoded Amino Acids |
| --- | --- | --- |
| Hydrophobic | | |
| Aromatic | F, Y, W, H | f, y, w, h, Phg, Nal, Thi, Tic, Pcf, Off, Mff, Pff, hPhe |
| Non-Polar | L, V, I, M, G, A, P | l, v, i, m, g, a, p, Bua, Bug, MeIle, Nle, MeVal, Cha, MeGly, Aib |
| Aliphatic | A, V, L, I | a, v, l, i, Dpr, Aib, Aha, MeGly, Bua, Bug, Mele, Cha, Nle, MeVal |
| Hydrophilic | | |
| Acidic | D, E | d, e |
| Basic | H, K, R | h, k, r, Dpr, Orn, hArg, Paf, Dbu, Dab |
| Polar | C, Q, N, S, T | c, q, n, s, t, Cit, AcLys, Mso, hSer |
| Small | G, A, V, C, N, S, T, D | g, a, v, c, n, s, t, d |

In the "core" peptides and peptide analogs of structure (II), the symbol "~" between each specified residue $X^n$ designates a backbone constitutive linking moiety. When the DR15 compounds of the invention are peptides, each "~" between the various $X^n$ represents an amide or peptide linkage of the following polarity: —C(O)—NH—. It is to be understood, however, that the DR15 compounds of the invention include analogs of peptides in which one or more amide or peptide linkages are replaced with a linkage other than an amide or peptide linkage, such as a substituted amide linkage, an isostere of an amide linkage, or a peptido or amide mimetic linkage. Thus, when used in connection with defining the various $X^n$ comprising the DR15 compounds of the invention, the term "residue" refers to the $C_\alpha$ carbon and side chain moiety(ies) of the designated amino acid or class of amino acid. As a specific example, defining $X^1$ as being a "Gly residue" means that $X^1$ is $C_\alpha H_2$. Defining $X^1$ as being an "Ala residue" means that $X^1$ is $C_\alpha HCH_3$ in which the $C_\alpha$ carbon is in either the D- or L-configuration. Defining $X^1$ as being an "A residue" means that $X^1$ is $C_\alpha HCH_3$ in which the $C_\alpha$ carbon is in the L-configuration.

Substituted amide linkages that may be included in the DR15 compounds of the invention include, but are not limited to, groups of the formula —C(O)NR², where R² is $(C_1-C_6)$ alkyl, $(C_5-C_{10})$ aryl, substituted $(C_5-C_{10})$ aryl, $(C_6-C_{16})$ arylalkyl, substituted $(C_6-C_{16})$ arylalkyl, 5-10 membered heteroaryl, substituted 5-10 membered heteroaryl, 6-16 membered heteroarylalkyl or substituted 6-16 membered heteroarylalkyl. In a specific embodiment, R² is $(C_1-C_6)$ alkanyl, $(C_2-C_6)$ alkenyl, $(C_2-C_6)$ alkynyl or phenyl.

Isosteres of amides that may be included in the DR15 compounds of the invention generally include, but are not limited to, —NR³—SO—, —NR³—S(O)₂—, —CH₂—CH₂—, —CH=CH— (cis and trans), —CH₂—NH—, —CH₂—S—, —CH₂—O—, —C(O)—CH₂—, —CH(OH)—CH₂— and —CH₂—S(O)₂—, where R³ hydrogen or R² and R² is as previously defined. These interlinkages may be included in the DR15 compounds of the invention in either the depicted polarity or in the reverse polarity. Peptide analogs including such non-amide linkages, as well as methods of synthesizing such analogs, are well-known. See, for example, Spatola, 1983, "Peptide Backbone Modifications," In: *Chemistry and Biochemistry of Amino Acids, Peptides and Proteins,* Weinstein, Ed., Marcel Dekker, New York, pp. 267-357 (general review); Morley, 1980, Trends Pharm. Sci. 1:463-468; Hudson et al., 1979, Int. J. Prot. Res. 14:177-185 (—CH₂—NH—, —CH₂—CH₂); Spatola et al., 1986, Life Sci. 38:1243-1249; Spatola, 1983, "Peptide Backbone Modifications: the Ψ [CH₂S] Moiety as an Amide Bond Replacement," In: *Peptides: Structure and Function V,* J. Hruby and D. H. Rich, Eds., Pierce Chemical Co., Rockford, Ill., pp. 341-344 (—CH₂—S—); Hann, 1982, J. Chem. Soc. Parkin Trans. I. 1:307-314 (—CH=CH—, cis and trans); Almquist et al., 1980, J. Med. Chem. 23:1392-1398 (—C(O)—CH₂—); European Patent Application EP 45665; Chemical Abstracts CA 97:39405 (—CH(OH)—CH₂—); Holladay et al., 1983, Tetrahedron Lett. 24:4401-4404 (—CH(OH)—CH₂—); and Hruby, 1982, Life Sci. 31:189-199 (—CH₂—S—).

Alternatively, one or more amide linkages may be replaced with peptidomimetic and/or amide mimetic moieties. Non-limiting examples of such moieties are described in Olson et al., 1993, J. Med. Chem. 36:3039-3049; Ripka & Rich, 1998, Curr. Opin. Chem. Biol. 2:441-452; Borchardt et al., 1997, Adv. Drug. Deliv. Rev. 27:235-256 and the various references cited therein.

While structure (II) contains 20 specified residue positions, it is to be understood that the DR15 compounds of the invention may contain fewer than 20 residues. Indeed, truncated forms of structure (II) containing as few as 8 residues that retain one or more of the utilities described herein are considered to be within the scope of the present invention. Truncated forms of the compounds of structure (II) are obtained by deleting one or more residues from either or both termini. Preferred truncated forms of structure (II) will contain at least 10 residues; more preferred truncated forms of structure (II) will contain at least 12 to 16 residues or more.

The core peptides or peptide analogs of structure (II) may also be extended at one or both termini. Typically, such extensions will range from about 1 to about 5 residues, but may be even longer, so long as the compound retains one or more of the utilities described herein. For example, one or both termini may be extended by 6, 7, 8, 9, 10 or even more residues.

In one embodiment of the invention, the extension has a sequence that corresponds to a sequence of a signal peptide capable of effecting transport across membranes, such that the DR15 compound is a "fusion polypeptide." Such fusion polypeptides are particularly advantageous for administering to cells DR15 compounds of the invention that may not readily traverse cell membranes. The signal sequence may be fused to either the N-terminal or C-terminal portion of the DR15 compound, depending upon the characteristics of the particular signal sequence selected. Signal sequences capable of transporting molecules into cells are well-known in the art. Any of these sequences may be used in connection with the DR15 compounds of the invention. Specific examples of such sequences include HIV Tat sequences (see, e.g., Fawell et al., 1994, Proc. Natl. Acad. Sci. USA 91:664; Frankel et al., 1988, Cell 55:1189; Savion et al., 1981, J. Biol. Chem. 256:1149; Derossi et al., 1994, J. Biol. Chem. 269:10444; Baldin et al., 1990, EMBO J. 9:1511; U.S. Pat. Nos. 5,804,604; 5,670,617; and 5,652,122, the disclosures of which are incorporated herein by reference), antennapedia sequences (see, e.g., Garcia-Echeverria et al., 2001, Bioorg. Med. Chem. Lett. 11:1363-1366; Prochiantz, 1999, Ann. NY Acad. Sci. 886:172-179; Prochiantz, 1996, Curr. Opin. Neurobiol. 6:629-634; U.S. Pat. No. 6,080,724, and the references cited in all of the above, the disclosures of which are incorporated herein by reference) and poly(Arg) or poly(Lys) chains of 5-10 residues. Additional non-limiting examples of specific sequences can be found in U.S. Pat. Nos. 6,248,558; 6,043,339; 5,807,746 6,251,398; 6,184,038 and 6,017,735, the disclosures of which are incorporated herein by reference.

The terminus of the DR15 compounds of the invention corresponding to the amino terminus, if present, may be in the "free" form (e.g., $H_2N-$), or alternatively may be acylated with a group of the formula $R^2C(O)-$ or $R^2S(O)_2-$, wherein $R^2$ is as previously defined. In one embodiment, $R^2$ is selected from the group consisting of $(C_1-C_6)$ alkyl, $(C_5-C_{10})$ aryl, $(C_6-C_{16})$ arylalkyl, 5-10 membered heteroaryl or 6-16 membered heteroarylalkyl. In a specific embodiment, the $R^2$ group is a group that facilitates entry of the DR15 compound into a cell. Such groups are well-known in the art.

In another embodiment, the amino terminus may be "blocked" with a blocking group designed to impart the DR15 compound with specified properties, such as a low antigenicity. Non-limiting examples of such blocking groups include polyalkylene oxide polymers such as polyethylene glycol (PEG). A variety of polymers useful for imparting compounds, and in particular peptides and proteins, with specified properties are known in the art, as are chemistries suitable for attaching such polymers to the compounds. Specific non-limiting examples may be found in U.S. Pat. Nos. 5,643,575; 5,730,990; 5,902,588; 5,919,455; 6,113,906; 6,153,655; and 6,177,087, the disclosures of which are incorporated herein by reference.

Of course, skilled artisans will appreciate that any of these transport-effecting, acylating and/or blocking groups may also be attached to a side chain moiety of a DR15 compound. Residues having appropriate functionalities for attaching such groups will be apparent to those of skill in the art, and include, by way of example and not limitation, Cys, Lys, Asp and Glu.

The terminus of the DR15 compounds corresponding to the C-terminus, if present, may be in the form of an underivatized carboxyl group, either as the free acid or as a salt, such as a sodium, potassium, calcium, magnesium salt or other salt of an inorganic or organic ion, or may be in the form of a derivatized carboxyl, such as an ester, thioester or amide. Such derivatized forms of the compounds may be prepared by reacting a DR15 compound having a carboxyl terminus with an appropriate alcohol, thiol or amine. Suitable alcohols, thiols or amines include, by way of example and not limitation, alcohols of the formula $R^2OH$, thiols of the formula $R^2SH$ and amines of the formula $R^2NH_2$, $R^2R^2NH$ or $NH_3$, where each $R^2$ is, independently of the others, as previously defined.

The C-terminus may also include transport-effecting or other blocking groups, such as those described above.

As will be recognized by skilled artisans, the various $X^n$ residues comprising the DR15 compounds of the invention may be in either the L- or D-configuration about their $C_\alpha$ carbons. In one embodiment, all of the $C_\alpha$ carbons of a particular DR15 compound are in the same configuration. In some embodiments of the invention, the DR15 compounds comprise specific chiralities about one or more $C_\alpha$ carbon(s) and/or include non-peptide linkages at specified locations so as to impart the DR15 compound with specified properties. For example, it is well-known that peptides composed in whole or in part of D-amino acids are more resistant to proteases than their corresponding L-peptide counterparts. Thus, in one embodiment, the DR15 compounds are peptides composed in whole or in part of D-amino acids. Alternatively, DR15 compounds having good stability against proteases may include peptide analogs including peptide linkages of reversed polarity at specified positions. For example, DR15 compounds having stability against tryptic-like proteases include peptide analogs having peptide linkages of reversed polarity before each L-Arg or L-Lys residue; DR15 compounds having stability against chymotrypsin-like proteases include peptide analogs having peptide linkages of reversed polarity before each small and medium-sized L-aliphatic residue or L-non-polar residue. In another embodiment, DR15 compounds having stability against proteases include peptide analogs composed wholly of peptide bonds of reversed polarity. Other embodiments having stability against proteases will be apparent to those of skill in the art. Additional specific embodiments of the DR15 compounds of the invention are described below.

The DR15 compounds of the invention can be in a linear form or a cyclic form, with or without branching. The cyclic forms can be cyclized via the terminal groups or via side chain groups on internal or terminal residues, through covalent or non-covalent linkages. Additional linking groups may also be present to facilitate cyclization.

In one specific embodiment, the DR15 compounds of the invention are 20-residue peptides or peptide analogs according to structural formula (III):

$$Z^3-X^1\sim X^2\sim X^3\sim X^4\sim X^5\sim X^6\sim X^7\sim X^8\sim X^9\sim X^{10}\sim X^{11}\sim X^{12}\sim X^{13}\sim X^{14}\sim X^{15}\sim X^{16}\sim X^{17}\sim X^{18}\sim X^{19}\sim X^{20}-Z^4 \quad \text{(III)}$$

wherein:
each $X^1$ through $X^{20}$ is as previously defined for structure (II);
$Z^3$ is $H_2N-$, $R^4HN-$ or $R^4C(O)NH-$;
$Z^4$ is $-C(O)O^-$, $-C(O)OR^4$, $-C(O)NHR^4$ or $-C(O)NH_2$;
each $R^4$ is independently $(C_1-C_6)$ alkyl or $(C_1-C_6)$ alkanyl;
each "~" is independently an amide linkage, a substituted amide linkage or an isostere of an amide linkage; and
each "—" represents a bond.

In another specific embodiment, the DR15 compounds of the invention are compounds according to structural formula (III) in which each "~" is an amide linkage.

In yet another specific embodiment, the DR15 compounds of the invention are compounds according to structural formula (III) in which:
- $X^1$ is a small aliphatic or a conformationally-constrained residue;
- $X^2$ is a small aliphatic or an acidic residue;
- $X^3$ is L-Arg;
- $X^4$ is L-Cys;
- $X^5$ is a small aliphatic or an aromatic residue;
- $X^6$ is a small aliphatic or a non-polar residue;
- $X^7$ is L-Arg;
- $X^8$ is L-Met;
- $X^9$ is L-Pro;
- $X^{10}$ is L-Pro;
- $X^{11}$ is L-Gln;
- $X^{12}$ is L-Ser;
- $X^{13}$ is L-Leu;
- $X^{14}$ is L-Ala;
- $X^{15}$ is L-Asp;
- $X^{16}$ is L-Ala;
- $X^{17}$ is a polar or a small aliphatic residue;
- $X^{18}$ is a small aliphatic or a non-polar residue.
- $X^{19}$ is L-Tyr;
- $X^{20}$ is L-Ser;
- $X^{21}$ is L-Val;
- $X^{22}$ is Gly;
- $X^{23}$ is L-Pro.

Preferably, $X^1$ is L-Pro or L-Ala, $X^2$ is L-Glu or L-Ala, $X^5$ is L-Tyr or L-Ala, $X^6$ is L-Met or L-Ala, $X^{17}$ is L-Gln or L-Ala and/or $X^{18}$ is L-Ile or L-Ala.

In another specific embodiment, the DR15 compounds of the invention include compounds according to structural formula IV, and variants of such compounds of formula IV in which 1, 2, 3 or 4, preferably 1 or 2, of the amino acid residues set forth in IV are substituted by another amino acid selected from the same class (as described herein) as the original amino acid or by an Ala or Gly residue:

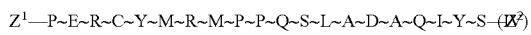

$Z^1$—P~E~R~C~Y~M~R~M~P~P~Q~S~L~A~D~A~Q~I~Y~S—($Z^2$)

wherein "—", "~", $Z^1$ and $Z^2$ are as defined previously for formula (I).

In still another specific embodiment, the DR15 compounds of the invention are selected from the group consisting of DR15wt (PERCYMRMPPQSLADAQIYS; SEQ ID NO:1), DR15PE (AARCYMRMPPQSLADAQIYS; SEQ ID NO:2), DR15QI (PERCYMRMPPQSLADAAAYS; SEQ ID NO:3) and DR15YM (PERCAARMPPQSLADAQIYS; SEQ ID NO: 4), and analogs and protease-resistant analogs thereof.

Active DR15 compounds of the invention are those that modulate, and in particular inhibit or downregulate, IL-4 induced IgE production and/or accumulation and/or processes associated therewith. The DR15 compounds of the invention may be assessed for such activity in any standard assay that assesses the ability of a compound to modulate IL-4 induced IgE production and/or accumulation. For example, a DR15 compound of the invention may be administered to a human or animal B-cell (e.g, primary B cells from blood, tonsils, spleens and other lymphoid tissues) stimulated with IL-4 (available from Pharmingen, Hamburg, Germany) and anti-CD40 mAbs (available from Ancell Corporation, Bayport Minn.) and the amount of IgE produced measured, for example, by an ELISA technique, such as the ELISA technique described in Worm et al., 1998, Blood 92:1713. The ELISA technique can use, for example, murine anti human IgE, biotinylated anti human IgE and streptavidin biotinylated horseradish peroxidase complex. Specific ELISA assays and techniques that may be used are provided in the Examples section. Particular active DR15 compounds include without limitation DR15wt (SEQ ID NO:1), DR15PE (SEQ ID NO:2), DR15QI (SEQ ID NO:3), or DR15YM (SEQ ID NO:4).

For DR15 compounds that readily traverse cell membranes, the compound may be administered to the cell by contacting the cell with the compound. DR15 compounds composed wholly of genetically-encoded amino acids that do not readily traverse cell membranes may be administered to the cell using well-known delivery techniques. In one embodiment, such DR15 compounds may be administered using well-known retroviral vectors and infection techniques pioneered by Richard Mulligan and David Baltimore with Psi-2 lines and analogous retroviral packaging systems based upon NIH 3T3 cells (see Mann et al., 1993, Cell 33:153-159, the disclosure of which is incorporated herein by reference). Such helper-defective packaging cell lines are capable of producing all of the necessary trans proteins (gag, pol and env) required for packaging, processing, reverse transcribing and integrating genomes. Those RNA molecules that have in cis the ψ packaging signal are packaged into maturing retrovirions. Virtually any of the art-known retroviral vectors and/or transfection systems may be used. Specific non-limiting examples of suitable transfection systems include those described in WO 97/27213; WO 97/27212; Choate et al., 1996, Human Gene Therapy 7:2247-2253; Kinsella et al., 1996, Human Gene Therapy 7:1405-1413; Hofmann et al., 1996, Proc. Natl. Acac. Sci. USA 93:5185-5190; Kitamura et al., 1995, Proc. Natl. Acac. Sci. USA 92:9146-9150; WO 94/19478; Pear et al., 1993, Proc. Natl. Acac. Sci. USA 90:8392-8396; Mann et al., 1993, Cell 33:153-159 and the references cited in all of the above, the disclosures of which are incorporated herein by reference. Specific non-limiting examples of suitable retroviral vector systems include vectors based upon murine stem cell virus (MSCV) as described in Hawley et al., 1994, Gene Therapy 1:136-138; vectors based upon a modified MFG virus as described in Rivere et al., 1995, Genetics 92:6733; pBABE as described in WO 97/27213 and WO 97/27212; and the vectors depicted in FIG. 11 of WO 01/34806, the disclosures of which are incorporated herein by reference. Other suitable vectors and/or transfection techniques are discussed in connection with gene therapy administration, infra.

A specific assay for assessing IL-4 induced IgE production that may be used to assay DR15 compounds of the invention is described in Worm et al., 2001, Int. Arch. Allergy Immunol. 124:233-236. Generally, a DR15 compound modulates IL-4 induced IgE production if it yields an increase or decrease in measured IgE levels of at least about 25% as compared to control cells (i.e., cells activated with IL-4+ anti-CD40 Mabs but not exposed to the DR15 compound). DR15 compounds that increase IL-4 induced IgE production are IgE agonists whereas DR15 compounds that decrease IL-4 induced IgE production are IgE antagonists. Skilled artisans will appreciate that DR15 compounds that inhibit greater levels of IL-4 induced IgE production, for example on the order of 50%, 60%, 70%, 80%, 90%, or even more as compared to control cells, are particularly desirable. Thus, while compounds that inhibit at least about 25% of IL-4 induced IgE production as compared to control cells are active, compounds that inhibit at least about 50%, 75% or even more IL-4 induced IgE production as compared to control cells are preferred.

In another embodiment, DR15 compounds may be assayed for the ability to modulate IL-4 induced transcription of a germline ε promoter. Generally, such assays involve administering a DR15 compound to an IL-4 induced cell comprising an IL-4 inducible germline ε promoter and assessing the amount of gene expression (i.e. transcription) downstream of the ε promoter. Depending upon the ability of the DR15 compound to traverse cell membranes, it may be administered to the cell by contacting the cell with the compound or (for peptide compounds) via the retroviral transfection techniques described supra. The amount of the downstream gene expression may be assessed at the mRNA level, for example by quantifying the amount of a downstream transcription product produced, or at the translation level, for example by quantifying the amount of a downstream translation product produced. In one embodiment, the germline ε promoter is operably linked to a reporter gene that encodes a protein that produces an observable and/or detectable signal, such as a fluorescent protein. Specific examples of suitable assays for assessing DR15 compounds for the ability to modulate germline ε transcription are described in U.S. Pat. No. 5,958,707, WO 01/34806, WO 99/58663, commonly owned copending application Ser. No. 09/712,821, filed Nov. 13, 2000 and commonly owned copending application Ser. No. 09/076,624, filed May 12, 1998, the disclosures of which are incorporated herein by reference. Generally, a DR15 compound modulates germline ε transcription if it yields an increase or decrease in measured downstream expression of at least about 25% as compared to control cells activated with IL-4 but not exposed to the DR15 compound. DR15 compounds that increase downstream expression are IL-4 agonists, whereas compounds that decrease (i.e. inhibit) downstream expression are IL-4 antagonists. Skilled artisans will appreciate that DR15 compounds that inhibit greater levels of IL-4 induced germline ε transcription, for example on the order of 50%, 60%, 70%, 80%, 90%, or even more as compared to control cells, are particularly desirable. Thus, while compounds that inhibit at least about 25% of IL-4 induced germline ε transcription as compared to control cells are active, compounds that inhibit at least about 50%, 75% or even more IL-4 induced germline ε transcription as compared to control cells are preferred. In one embodiment of the invention, active DR15 compounds are those that exhibit a reporter ratio of ≧1.1 in the A5T4 reporter line screening assay described in the examples section. In general, the "reporter ratio" is the ratio of the signal from a reporter under control of the ε promoter in the absence of a DR15 compound to that in the presence of the DR15 compound. In particular, for screening in the A5T4 reporter line that has been transformed with the inhibitor peptide vector, the reporter ratio can be determined from the ratio of the GFP fluorescence of IL-4 stimulated cells in the presence of doxycycline or tetracycline (i.e., when expression of the peptide is repressed) to the GFP fluorescence of IL-4 stimulated cells in the absence of doxycycline or tetracycline.

As mentioned previously, B-cells initially produce IgD and IgM immunoglobulins and, when induced by the proper cytokines, produce IgEs. B-cells can be induced to produce other types of immunoglobulins, such as IgGs and IgAs, as well. For example, in the presence of the cytokine interleukin-2 (IL-2), B-cells produce IgG1; in the presence of a combination of IL-2 and TGF-β, B-cells produce IgA. In many situations, it is desirable to selectively modulate (increase or decrease) the production of a single immunoglobulin isotype, as such specificity permits the ability to treat or prevent diseases associated with the production and/or accumulation of the specified immunoglobulin isotype without affecting the immune system generally. Thus, in one embodiment, the DR15 compounds specifically modulate IL-4 induced germline ε transcription or IL-4 induced IgE production and/or accumulation. By "specific" is meant that the DR15 compound modulates IL-4 induced IgE production and/or accumulation or IL-4 induced germline ε transcription but does not significantly affect the production and/or accumulation of another immunoglobulin, or transcription of the promoter of another Ig isotype. In a particular embodiment, a DR15 compound specifically inhibits IL-4 induced germline ε transcription or IL-4 induced IgE production or accumulation. Such DR15 compound does not significantly inhibit production and/or accumulation of another Ig isotype, or transcription of another Ig isotype promoter, if the observed inhibition of the other Ig isotype in an appropriate assay is on the order of 10% or less as compared to control cells. Such specificity may be with respect to a single Ig isotype, or may be with respect to one or more Ig isotypes. For example, a DR15 compound may be assessed for specificity by assaying its ability to inhibit, for example, IgA production and/or accumulation or to inhibit germline α transcription in assays similar to those described above, except that the cells are activated with effectors suitable for IgA switching and synthesis and amount of IgA produced or the amount of expression downstream of a germline α promoter is assessed. Specific, non-limiting examples of DR15 compounds that specifically inhibit IL-4 induced IgE production and/or IL-4 induced germline ε transcription include peptides DR15wt (SEQ ID NO:1), DR15PE (SEQ ID NO:2), DR15QI (SEQ ID NO:3), or DR15YM (SEQ ID NO:4).

As will be discussed in more detail below, it has been discovered that the ability of certain DR15 compounds to inhibit IL-4 induced IgE production and/or IL-4 induced germline ε transcription is mediated by binding a thioredoxin-like 32 kDa protein (TXNL). Accordingly, DR15 compounds may also be assessed for activity based upon their ability to bind an TXNL using, for example, any of the TXNL binding assays described infra. Generally, active DR15 compounds are those having a binding constant (Kd) on the order of 10 mM or less, with Kds in the range of 100 μM, 10 μM, 1 μM, 100 nM, 10 nM, 1 nM or even lower, being preferred. Alternatively, active DR15 compounds are those that compete for binding a TXNL with another active DR15 compound. In a specific embodiment, the DR15 compound competes for binding a TXNL with peptide DR15wt (SEQ ID NO:1), peptide DR15PE (SEQ ID NO:2), peptide DR15QI (SEQ ID NO:3), or peptide DR15YM (SEQ ID NO:4). The ability of a DR15 compound to compete for binding an TXNL with another DR15 compound may be assessed using conventional competitive binding assay techniques. Generally, active DR15 compounds are those that exhibit an $IC_{50}$ in the range of 1 mM or lower, with $IC_{50}$s in the range of 100 μM, 10 μM, 1 μM, 100 nM, 10 nM, 1 nM or even lower, in such competitive binding assays being preferred.

Chemical Synthesis of the DR15 Compounds

DR15 compounds of the invention may be prepared using standard techniques of organic synthesis. DR15 compounds that are peptides may be prepared using conventional stepwise solution or solid phase synthesis (see, e.g., *Chemical Approaches to the Synthesis of Peptides and Proteins*, Williams et al., Eds., 1997, CRC Press, Boca Raton Fla., and references cited therein; *FMOC Solid Phase Peptide Synthesis: A Practical Approach,* Chan & White, Eds., 2000, IRL Press, Oxford, England, and references cited therein).

Alternatively, DR15 compounds, may be prepared by way of segment condensation, as described, for example, in Liu et al., 1996, Tetrahedron Lett. 37(7):933-936; Baca et al., 1995, J. Am. Chem. Soc. 117:1881-1887; Tam et al., 1995, Int. J. Peptide Protein Res. 45:209-216; Schnolzer and Kent, 1992, Science 256:221-225; Liu and Tam, 1994, J. Am. Chem. Soc. 116(10):4149-4153; Liu and Tam, 1994, Proc. Natl. Acad. Sci. USA 91:6584-6588; Yamashiro and Li, 1988, Int. J. Peptide Protein Res. 31:322-334. The condensation technique is particularly useful for synthesizing DR15 compounds comprising Gly residues. Other methods useful for synthesizing the DR15 compounds of the invention are described in Nakagawa et al., 1985, J. Am. Chem. Soc. 107:7087-7092. DR15 compounds that are peptide analogs may be synthesized using the various methods described in the references cited in connection with amide isosteres and amide and peptidomimetics, supra.

DR15 compounds containing N- and/or C-terminal blocking groups can be prepared using standard techniques of organic chemistry. For example, methods for acylating the N-terminus of a peptide or amidating or esterifying the C-terminus of a peptide are well-known in the art. Modes of carrying other modifications at the N- and/or C-terminus will be apparent to those of skill in the art, as will modes of protecting any side-chain functionalities as may be necessary to attach terminal blocking groups.

Formation of disulfide linkages, if desired, is generally conducted in the presence of mild oxidizing agents. Chemical oxidizing agents may be used, or the compounds may simply be exposed to atmospheric oxygen to effect these linkages. Various methods are known in the art, including those described, for example, by Tam et al., 1979, Synthesis 955-957; Stewart et al., 1984, Solid Phase Peptide Synthesis, 2d Ed., Pierce Chemical Company Rockford, Ill.; Ahmed et al., 1975, J. Biol. Chem. 250:8477-8482; and Pennington et al., 1991 Peptides 1990 164-166, Giralt and Andreu, Eds., ESCOM Leiden, The Netherlands. An additional alternative is described by Kamber et al., 1980, Helv. Chim. Acta 63:899-915. A method conducted on solid supports is described by Albericio, 1985, Int. J. Peptide Protein Res. 26:92-97. Any of these methods may be used to form disulfide linkages in the DR15 compounds of the invention.

Cyclic peptides may be prepared or may result from the formation of single or multiple disulfide bonds, other sidechains or head-to-tail cyclizations, either directly or by way of an optional linker. The cyclic peptides may be prepared using any art-known techniques for the preparation of cyclic peptides and cyclic peptide analogs. For example, the peptide or peptide analog may be prepared in linear or noncyclized form using conventional solution or solid phase peptide and/or peptide analog syntheses and cyclized using standard chemistries. The linear polypeptides can be cyclized with a linking group between the two termini, between one terminus and the side chain of an amino acid in the peptide or peptide derivative, or between the side chains to two amino acids in the peptide or peptide derivative. Suitable procedures for synthesizing the peptide and peptide analogs described herein, as well as suitable chemistries for cyclizing such compounds, are well known in the art. For references related to synthesis of cyclic peptides the reader is referred to Tam et al., 2000, Biopolymers 52:311-332; Camamero et al, 1998, Angew. Chem. Intl. Ed. 37: 347-349; Tam et al., 1998, Prot. Sci. 7:1583-1592; Jackson et al., 1995, J. Am. Chem.Soc. 117:819-820; Dong et al., 1995, J. Am. Chem. Soc. 117:2726-2731; Ishida et al., 1995, J. Org. Chem. 60:5374-5375; WO 95/33765, published Jun. 6, 1995; Xue and DeGrado, 1994, J. Org. Chem. 60(4):946-952; Jacquier et al., 1991, In: Peptides 1990 221-222, Giralt and Andreu, Eds., ESCOM Leiden, The Netherlands; Schmidt and Neubert, 1991, In: Peptides 1990 214-215, Giralt and Andreu, Eds., ESCOM Leiden, The Netherlands; Toniolo, 1990, Int. J. Peptide Protein Res. 35:287-300; Ulysse et al., 1995, J. Am. Chem. Soc. 117:8466-8467; Durr et al., 1991, Peptides 1990 216-218, Giralt and Andreu, Eds., ESCOM Leiden, The Netherlands; Lender et al., 1993, Int. J. Peptide Protein Res. 42:509-517; Boger and Yohannes, 1990, J. Org. Chem. 55:6000-6017; Brady et al., 1979, J. Org. Chem. 4(18):3101-3105; Spatola et al., 1986, J. Am. Chem. Soc. 108:825-831; Seidel et al., 1991, In: Peptides 1990 236-237, Giralt and Andreu, Eds., ESCOM Leiden, The Netherlands; Tanizawa et al., 1986, Chem. Phar, Bull. 34(10):4001-4011; Goldenburg & Creighton, 1983, J. Mol.Biol. 165:407-413; WO 92/00995 and WO 94/15958. These methods may be routinely adapted to synthesize the cyclic compounds of the invention and are incorporated into this application by reference.

Recombinant Synthesis of the DR15 Compounds

If the DR15 compound is composed entirely of genetically-encoded amino acids, or a portion of it is so composed, the peptide or the relevant portion may also be synthesized using conventional recombinant genetic engineering techniques.

For recombinant production, a polynucleotide sequence encoding the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Sambrook et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. each of which is incorporated by reference herein in its entirety.)

To increase efficiency of production, the polynucleotide can be designed to encode multiple units of the peptide separated by enzymatic cleavage sites—either homopolymers (repeating peptide units) or heteropolymers (different peptides strung together) can be engineered in this way. The resulting polypeptide can be cleaved (e.g., by treatment with the appropriate enzyme) in order to recover the peptide units. This can increase the yield of peptides driven by a single promoter. In a preferred embodiment, a polycistronic polynucleotide can be designed so that a single mRNA is transcribed which encodes multiple peptides (i.e., homopolymers or heteropolymers) each coding region operatively linked to a cap-independent translation control sequence; e.g., an internal ribosome entry site (IRES). When used in appropriate viral expression systems, the translation of each peptide encoded by the mRNA is directed internally in the transcript; e.g., by the IRES. Thus, the polycistronic construct directs the transcription of a single, large polycistronic mRNA which, in turn, directs the translation of multiple, individual peptides. This approach eliminates the production and enzymatic processing of polyproteins and may significantly increase yield of peptide driven by a single promoter.

Polynucleotides capable of generating or expressing certain cyclic peptide embodiments of the compounds of the invention may be prepared in vitro and/or in vivo. Polypeptides may be prepared from polynucleotides to generate or express the cyclic peptides utilizing the trans splicing ability of split inteins. Methods for making such polynucleotides to yield cyclic peptides are known in the art and are described, for example, in WO 01/66565, WO 00/36093; U.S. Patent Application No. 60/358,827, entitled "Cyclic Peptides and Analogs Useful to Treat Allergies", filed on Feb. 21, 2002, the disclosures of which are incorporated herein by reference.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp 17.5-E or hsp 17.3-B (Gurley et al., 1986, Mol. Cell. Biol. 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, N.Y., Section VIII, pp. 421-463; and Grierson & Corey, 1988, Plant Molecular Biology, 2d Ed., Blackie, London, Ch. 7-9.

In one insect expression system that may be used to produce the peptides of the invention, *Autographa californica,* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed (e.g., see Smith et al., 1983, J. Virol. 46:584; U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., see Logan & Shenk, 1984, Proc. Natl. Acad. Sci. USA 81:3655-3659). Alternatively, the vaccinia 7.5 K promoter may be used, (see, e.g., Mackett et al., 1982, Proc. Natl. Acad. Sci. USA 79:7415-7419; Mackett et al., 1984, J. Virol. 49:857-864; Panicali et al., 1982, Proc. Natl. Acad. Sci. USA 79:4927-4931).

Other expression systems for producing DR15 peptides of the invention will be apparent to those having skill in the art.

Purification Of DR15 Compounds

The DR15 compounds of the invention can be purified by art-known techniques such as reverse phase chromatography high performance liquid chromatography, ion exchange chromatography, gel electrophoresis, affinity chromatography and the like. The actual conditions used to purify a particular compound will depend, in part, on synthesis strategy and on factors such as net charge, hydrophobicity, hydrophilicity, etc., and will be apparent to those having skill in the art.

For affinity chromatography purification, any antibody which specifically binds the compound may be used. For the production of antibodies, various host animals, including but not limited to rabbits, mice, rats, etc., may be immunized by injection with a compound. The compound may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*bacilli* Calmette-Guerin) and *Corynebacterium parvum*.

Monoclonal antibodies to a compound may be prepared using any technique which provides for the production of antibody molecules by continuous cell lines in culture. These include, but are not limited to, the hybridoma technique originally described by Kohler & Milstein, 1975, Nature 256:495-497 and/or Kaprowski, U.S. Pat. No. 4,376,110; the human B-cell hybridoma technique described by Kosbor et al., 1983, Immunology Today 4:72 and/or Cote et al., 1983, Proc. Natl. Acad. Sci. USA 80:2026-2030; and the EBV-hybridoma technique described by Cole et al., 1985, Monoclonal Antibodies and Cancer Therapy, Alan R. Liss, Inc., pp. 77-96. In addition, techniques developed for the production of "chimeric antibodies" (Morrison et al., 1984, Proc. Natl. Acad. Sci. USA 81:6851-6855; Neuberger et al., 1984, Nature 312:604-608; Takeda et al., 1985, Nature 314:452-454; Boss, U.S. Pat. No. 4,816,397; Cabilly, U.S. Pat. No. 4,816,567) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089). Alternatively, techniques described for the production of single chain antibodies (see, e.g., U.S. Pat. No. 4,946,778) can be adapted to produce compound-specific single chain antibodies.

Antibody fragments which contain deletions of specific binding sites may be generated by known techniques. For example, such fragments include but are not limited to F(ab')2 fragments, which can be produced by pepsin digestion of the antibody molecule and Fab fragments, which can be generated by reducing the disulfide bridges of the F(ab')2 fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, Protein Purification: Principles and Practice, Springer-Verlag New York, Inc., N.Y., Livingstone, 1974, Methods In Enzymology: Immunoaffinity Chromatography of Proteins 34:723-731.

As will be recognized by skilled artisans, the above methods may also be used to prepare anti-TXNL antibodies. Such anti-TXNL antibodies may be used in the various methods described herein, for example, to inhibit IL-4 induced isotype switching and/or IgE production and/or to inhibit IL-4 induced germline ε transcription. Such antibodies may also be used in the various therapeutic methods described herein.

Screening Assays

The present inventors have discovered that the IgE regulatory effects of four DR15 compounds of the invention, peptides DR15wt (SEQ ID NO:1), DR15PE (SEQ ID NO:2), DR15QI (SEQ ID NO:3), and DR15YM (SEQ ID NO:4), are mediated by a TXNL. Specifically, the present inventors have discovered that these four DR15 compounds bind a hTXNL in yeast two hybrid (YTH) assays in a manner that correlates with their ability to inhibit IL-4 induced germline c transcription in in vitro cellular assays.

Human TXNL is a novel member of the thioredoxin superfamily (Miranda-Vizuete A. et al., 2000, DNA Sequ. 10(6):419-24). Thioredoxins (Trx), are a group of small ubiquitous proteins of approximately 100 amino acid residues (12 kDa), and are characterized by an amino acid sequence of the active site, -Cys-Gly-Pro-Cys-. Thioredoxin can exits in either a reduced form or an oxidized form via the reversible oxidation of the active site disulfide bond. In its oxidized form, the two cysteine residues of Trx are linked by an intramolecular disulfide bond. Oxidized thioredoxin ($Trx-S_2$) can be reduced by NADPH and the flavoenzyme thioredoxin reductase (TR) in vivo, the so-called thioredoxin system (Reaction 1) (Holmgren, A., 1985, Annu. Rev. Biochem. 54, 237-271). Reduced thioredoxin ($Trx-(SH)_2$) contains two thiol groups and can efficiently catalyze the reduction the disulfide bridge ($S_2$) of target proteins (Reaction 2).

TR

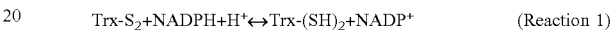

$$Trx\text{-}S_2 + NADPH + H^+ \leftrightarrow Trx\text{-}(SH)_2 + NADP^+ \quad \text{(Reaction 1)}$$

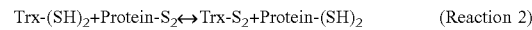

$$Trx\text{-}(SH)_2 + Protein\text{-}S_2 \leftrightarrow Trx\text{-}S_2 + Protein\text{-}(SH)_2 \quad \text{(Reaction 2)}$$

Therefore, the primary cellular function of Trx is to reduce other proteins via the reversible oxidation and reduction of the two cysteine residues in the active site. (Lee et al., J. Biol. Chem (1998) 273:19160-19166).

Trx is ubiquitously present and is evolutionarily conserved from prokaryotes to higher eukaryotes, plants, and animals (Holmgren, A., 1984, Methods Enzymol. 107, 295-300, Holmgren A., 1985, supra; Holmgren A., 1989, J. Biol. Chem. 264, 13963-13966). In eukaryotic cells, Trx has been implicated in a wide variety of biochemical and biological functions. For example, in eukaryotic cells, Trx can function as a hydrogen donor for ribonucleotide reductase RNR, 3-phosphoadenosine 5-phosphosulfate, and methionine sulfoxide reductases, similar to the prokaryotic Trx (Holmgren A, 1985, supra). It can also function as a hydrogen donor (Tsang et al., 1976, J. Bacteriol, 125, 923-933) and an essential subunit of T7 DNA polymerase (Lim et al., 1985, J. Bacteriol., 161, 799-802). In addition, Trx can facilitate refolding of disulfide-containing proteins (Lundstrom et al., 1990, J. Biol. Chem. 265, 9114-9120); activate the interleukin-2 receptor (Tagaya et al., 1989, EMBO J. 8, 757-764); and modulate the DNA binding activity of some transcription factors, e.g. NF-kappa B (Matthews, et al., 1992, Nucleic Acids Res. 20, 3821-3830), AP-1 (Schenk et al., 1994, Proc. Natl. Acad. Sci. U.S.A. 91, 1672-1676), p53 and PEBP-2 (Tanaka et al., Free Radic Res December 2001; 33(6):851-855). Thioredoxin acts as an antioxidant able to reduce hydrogen peroxide (Spector et al., 1988, J. Biol. Chem. 263, 4984-4990), scavenge free radicals (Schallreuter et al.,1986 Biochem. Biophys. Res. Commun. 136, 630-637), and protect cells against oxidative stress (Nakamura et al., 1994, Immunology Lett. 42, 75-80). Thioredoxin also plays a role in growth stimulation of human T cells. Adult T cell leukemia-derived factor, which augments the expression of interleukin-2 receptor, was found to be identical to human Trx ("hTrx") (Tagaya et al., 1989, EMBO J. 8, 757-764). Additionally, Trx reportedly inhibits the expression of human immunodeficiency virus in macrophages (Newman et al., 1994, J. Exp. Med. 180, 359-363).

Human TXNL is a novel member of the expanding thioredoxin superfamily. Human TXNL (hTXNL) contains two distinct domains: an N-terminal Trx-like domain containing the active site (Cys-Gly-Pro-Cys) and a novel C-terminal domain of 184-residues not found in Trxs. (Lee et al., 1998, supra). The N-terminal 100 amino acids of hTXNL has 43% identity to hTrx and has 26-29% identity to the Trx-like domains of other Trx-related proteins such as Rat TRX2, nucleoredoxin, and human PDI (Lee et al., 1998, supra). NCBI Blast search of the N-terminal 100 amino acids of hTXNL revealed 67 amino acids with a 100% identity to a portion of a 1026 amino acid human protein similar to WD repeat domain 7 (NCBI gi|18589130|ref|XP_028588.3|).

Human TXNL is ubiquitously expressed in human tissues and cell lines and is localized in the cytoplasm (Lee et al., 1998, supra). In human thymoma HBP-ALL cells, hTXNL co-purifies with the catalytic fragment of a kinase of the STE20 family which is proteolytically activated by caspases during apoptosis. (Lee et al., 1998, supra). However, no cellular function of has yet been assigned to hTXNL (Miranda-Vizuete et al., 2000, DNA Seq 10(6):419-24). Recently, the 12 kDa Trx-like domain of hTXNL, consisting of 105 amino acids was crystallized (Chen et al., 2001, Acta Crystallogr D Biol Crystalogr 57(pt11): 1712-4).

Despite the similarity of Trx and hTXNL with respect to the catalytic site, some functional and structural differences have been observed. First, mammalian Trx contains three conserved noncatalytic cysteine residues in addition to the two cysteine residues in the active site. These cysteine residues, $Cys^{62}$, $Cys^{69}$, and $Cys^{73}$, in hTrx can reportedly undergo oxidation, which leads to inactivation and dimerization of thioredoxin (Ren, X et al., 1993, Biochemistry 32, 9701-9708). In contrast, the N-terminal domain of hTXNL has only one extra cysteine residue, $Cys^{64}$, corresponding to the $Cys^{62}$ of hTrx (Miranda-Vizuete et al., 2000, supra). Thus, the reducing activity of hTXNL may be differently regulated from mammalian Trx. Secondly, while the isolated N-terminal domain of hTXNL showed some reducing activity for insulin disulfide bonds, full-length hTXNL has no reducing activity in the same assay, suggesting that C-terminal region of hTXNL may modulate the reducing activity (Miranda-Vizuete et al., 2000, supra). Thirdly, homologous thioreductases have been reported to activate some proteins with thioredoxin-like domains in the insulin assay (Kurooka et al., 1997, Genomics, 39(3):331-9.) However, hTXNL is not a substrate of human thioredoxin reductase (hTR) (Miranda-Vizuete et al., 1998, supra). It has been postulated that certain amino acid substitutions account for the inability of hTXNL to be reduced by the physiological redundant thioreductase. For instance, the negatively charged Asp26 (all numbering referred to hTrx), which participates in the charge stabilization of the active site is changed to a positively charged Lys residue in hTXNL. (Miranda-Vizuete et al., 2000, DNA Seq 10(6):419-24). In hTrx, Ala29 interacts by Van De Walls contact to Trp31 to stabilize the active site surface (Eklund, K. et al., 1991, Proteins: Structure Function and Genetics, 11, 13-18). In hTXNL, these two residues are changed to Met and Gly, respectively (Miranda-Vizuete et al., 2000, supra). On the other side of the CGPC active site, the positively charged Lys36, that stabilizes the thiolate in the active site, is changed to a Leu residue in hTXNL and thus unable to stabilize the thiolate intermediate. Collectively, these studies suggest that cellular function of hTXNL may not be dependent on its redox capacities (Miranda-Vizuete et al., 2000, supra).

While no cellular function of has yet been assigned to hTXNL in the literature, the present inventors are the first to discover a link between hTXNL and modulation of the IL-4 signaling cascade involved in the production of IgE, and in particular to IL-4 induced isotype switching of B-cells to produce IgE.

This significant discovery enables, for the first time, the ability to use a TXNL as a "surrogate" analyte in simple binding assays to screen for and/or identify compounds involved in IL-4 induced IgE regulation. Such compounds are useful in the treatment and/or prevention of diseases caused by or associated with IgE production and/or accumulation, such as anaphylactic hypersensitivity or allergic reactions and/or symptoms associated with such reactions, allergic rhinitis, allergic conjunctivitis, systemic mastocytosis, hyper IgE syndrome, IgE gammopathies, atopic disorders such as atopic dermatitis, atopic eczema and/or atopic asthma, and B-cell lymphoma.

Thus, the invention also provides methods and kits useful for identifying compounds having specified utilities. In specific embodiments, the methods and kits may be used to identify compounds that inhibit IL-4 induced IgE production and/or accumulation, compounds that inhibit IL-4 induced isotype switching of B-cells to produce IgE, compounds that inhibit IL-4 induced germline ε transcription, and/or compounds useful to treat or prevent diseases caused by or associated with IgE production and/or accumulation, such as those described above.

"Thioredoxin-like 32 kDa proteins" or "TXNLs" useful in the screening methods and kits of the invention include any protein recognized in the art as belonging to the thioredoxin-like 32 kDa family. In particular, useful TXNLs include human TXNL ("hTXNL") (NCBI Sequence Database #NP_004777, encoded by nucleotide sequence #NM_004786, inter alia), shown in FIG. 10 as SEQ ID NO: 5, and allelic and species variants thereof, as well as fragments and fusions thereof that bind DR15 compounds, particularly DR15wt . Typically, such proteins will have polypeptide sequences that share at least about 80% identity at the amino acid level with hTXNL. In addition, TXNLs useful in the screening methods will bind the DR15 compounds of the invention, in particular peptide DR15wt (SEQ ID NO:1). Preferably, the TXNL employed in the methods of the present invention will have at least 85%, 90%, 95% or even higher % identity with hTXNL. Specific examples of TXNLs suitable for use in the methods and kits of the invention include TXNL derived from human TXNL described by Miranda-Vizuete, et al., 1998, supra; Lee, et al., 1998, supra), as well as the various corresponding mammalian homologs thereof (for example, *Rattus norvegicus,* and *Mus Musculus,* etc.). The amino acid sequences of these various TXNLs, as well as the sequences of nucleic acid molecules encoding these TXNLs, are known in the art and can be found in the following references and/or NCBI (GenBank) entries: *Rattus norvegicus* thioredoxin-related protein (Tang et al., Direct Submission, 4 Apr. 1999, NCBI gi|15430626|gb|AAK98516.1) *Mus Musculus* thioredoxin-related protein (Lee et al, 1998, supra; Lee et al., Direct Submission (8 Mar. 1998, NCBI gi|2970691|gb|AAC40183.1).

As will be recognized by skilled artisans, mutants and/or fragments of a TXNL may also be used in the assays and kits of the invention. Mutants or fragments that are useful in this regard are those which bind an active DR15 compound, preferably peptide DR15wt (SEQ ID NO:1), peptide DR15PE (SEQ ID NO:2), peptide DR15QI (SEQ ID NO:3), or peptide DR15YM (SEQ ID NO:4). Suitable fragments include TXNLs that are truncated at the N- and/or C-terminus by one or more amino acids, typically by about 1 to 10-20 amino acids, although fragments truncated by more amino acids may be used, provided the fragments bind an active DR15 compound. Additionally, mutants and/or fragments of TXNL that substantially retain one or more of the biological activities of TXNL are useful in the assays and kits of the invention. By "substantially retain" is meant that the mutant or fragment has at least 10% of the biological activity of TXNL as measured by any conventional assay of TXNL activity; preferably, the mutant or fragment has at least 50% of the biological activity of TXNL.

TXNL mutants useful in the methods and kits of the invention include conservative mutants in which one or more amino acids is replaced with another amino acid of the same category, as described above. Of course TXNL mutants including non-conservative substitutions may also be used, so long as the particular mutant binds an active DR15 compound and/or substantially retains TXNL activity. Thus, unless indicated otherwise, the expression "thioredoxin-like 32 kDa protein" or "TXNL" as used herein specifically includes such mutants and/or fragments in addition to the full-length wild-type proteins.

The TXNLs may be obtained using conventional recombinant and purification techniques or may be isolated directly from the natural source. For example, any of the recombinant techniques discussed supra in connection with the DR15 compounds may be used to produce a TXNL suitable for use in methods and kits of the invention. Such recombinantly-produced TXNLs may be isolated using affinity chromatography (for example with an anti-TXNL antibody other conventional techniques. Specific examples that may be routinely adapted are described in Lee et al., 1998, supra and Chen et al., 2001, supra, the disclosures of which are incorporated herein by reference. Other techniques for obtaining TXNLs for use in the methods and kits of the invention will be apparent to those of skill in the art.

Any screening technique known in the art for determining whether compounds bind one another can be used to screen for compounds that bind a TXNL. The compounds screened can range from small organic molecules to large polymers and biopolymers, and can include, by way of example and not limitation, small organic compounds, saccharides, carbohydrates, polysaccharides, lectins, peptides and analogs thereof, polypeptides, proteins, antibodies, oligonucleotides, polynucleotides, nucleic acids, etc. In one embodiment, the candidate compounds screened are small organic molecules having a molecular weight in the range of about 100-2500 daltons. Such candidate molecules will often comprise cyclical structures composed of carbon atoms or mixtures of carbon atoms and one or more heteroatoms and/or aromatic, polyaromatic, heteroaromatic and/or polyaromatic structures. The candidate agents may include a wide variety of functional group substituents. In one embodiment, the substituent(s) are independently selected from the group of substituents known to interact with proteins, such as, for example, amine, carbonyl, hydroxyl and carboxyl groups.

The candidate compounds may be screened on a compound-by-compound basis or, alternatively, using one of the myriad library techniques commonly employed in the art. For example, synthetic combinatorial compound libraries, natural products libraries and/or peptide libraries may be screened using the assays of the invention to identify compounds that bind a TXNL. The candidate compounds may be assessed for the ability to bind a TXNL per se, or they may be assessed for the ability to competitively bind a TXNL in the presence of an active DR15 compound of the invention, such as peptide DR15wt (SEQ ID NO:1), peptide DR15PE (SEQ ID NO:2), peptide DR15QI (SEQ ID NO:3), or peptide DR15YM (SEQ ID NO:4), or another compound that competitively binds an TXNL in the presence of an active DR15 compound of the invention. These competitive binding assays can identify compounds that bind the TXNL at approximately the same site as the active DR15 compound. Myriad techniques for carrying out competitive binding assays are known in the art. Any of these techniques may be employed in the present invention.

Such binding experiments may be conducted wholly in solution or, alternatively, either the TXNL or the candidate compound may be immobilized on a solid support. For example, the TXNL or the candidate compound may be attached to a glass or other bead or a solid surface such as, for example, the bottom of a petri dish. The immobilization may be mediated by non-covalent interactions or by covalent interactions. Methods for immobilizing myriad types of compounds and proteins on solid supports are well-known. Any of these methods may be used to immobilize the TXNL and/or candidate compound on solid supports.

The binding assays may employ a purified TXNL or, alternatively, the assays may be carried out with nucleosol and/or cytosol fractions from cells that express the TXNL, either endogenously or recombinantly.

Whether carried out in solution or with an immobilized TXNL or candidate compound, the TXNL and candidate compound are typically contacted with one another under conditions conducive to binding. Although the actual conditions used can vary, typically the binding assays are carried out under physiological conditions. The concentrations of TXNL and candidate compound used will depend upon, among other factors, whether the TXNL or candidate compound is immobilized or free in solution, the binding affinities of candidate compounds, etc. Actual concentrations suitable for a particular assay will be apparent to those of skill in the art.

In many embodiments of the kits and assays of the invention it may be convenient to employ a labeled TXNL and/or labeled candidate compound. For example, in one convenient embodiment, binding is assessed by contacting an immobilized candidate compound with a labeled TXNL and assaying for the presence of immobilized label. For such embodiments, the label may be a direct label, i.e., a label that itself is detectable or produces a detectable signal, or it may be an indirect label, i.e., a label that is detectable or produces a detectable signal in the presence of another compound. The method of detection will depend upon the labeled used, and will be apparent to those of skill in the art.

Examples of suitable direct labels include radiolabels, fluorophores, chromophores, chelating agents, particles, chemiluminescent agents and the like. Suitable radiolabels include, by way of example and not limitation, $^3$H, $^{14}$C, $^{32}$P, $^{35}$S, $^{36}$Cl, $^{57}$Co, $^{58}$Co, $^{59}$Fe, $^{90}$Y, $^{125}$I, $^{131}$I and $^{186}$Re. Suitable fluorophores include, by way of example and not limitation, fluorescein, rhodamine, phycoerythrin, Texas red, free or chelated lanthanide series salts such as Eu$^{3+}$ and the myriad fluorophores available from Molecular Probes Inc., Eugene, Oreg. Examples of suitable colored labels include, by way of example and not limitation, metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as those described Snyder (EP 0 280 559 and 0 281 327) and dyes encapsulated in liposomes as described by Campbell et al. (U.S. Pat. No. 4,703,017). Other direct labels that may be used will be apparent to those of skill in the art.

Examples of suitable indirect labels include enzymes capable of reacting with or interacting with a substrate to produce a detectable signal (such as those used in ELISA and EMIT immunoassays), ligands capable of binding a labeled moiety, and the like. Suitable enzymes useful as indirect labels include, by way of example and not limitation, alkaline phosphatase, horseradish peroxidase, lysozyme, glucose-6-phosphate dehydrogenase, lactate dehydrogenase and urease. The use of these enzymes in ELISA and EMIT immunoassays is described in detail in Engvall, 1980, Methods in Enzymology, 70:419-439 and U.S. Pat. No. 4,857,453.

Methods of labeling proteins and compounds with a variety of labels such as those described above are well-known. Any of these methods may be used to label TXNLs and/or candidate compounds. For example, an TXNL may be labeled with a fluorophore such as fluorescein by incubating the TXNL with, for example, fluorescein isothiocyanate, using conventional techniques. Alternatively, a TXNL (or a candidate compound produced by recombinant techniques) can be labeled metabolically by culturing cells that express the TXNL in the presence of culture medium supplemented with a metabolic label, such as, by way of example and not limitation, [$^{35}$S]-methionine, one or more [$^{14}$C]-labeled amino acids, one or more [$^{15}$N]-labeled amino acids and/or [$^{3}$H]-labeled amino acids (with the tritium substituted at non-labile positions).

In one embodiment of the invention, candidate compounds may be screened for the ability to bind a TXNL using an affinity chromatography technique. For example, a TXNL may be attached to a chromatography resin according to standard techniques to create a TXNL affinity resin and this TXNL affinity resin used to identify compounds that bind the resin. Alternatively, the candidate compound could be bound to the resin and the resin used to determine whether it binds a TXNL. In another alternative embodiment, an active DR15 compound of the invention may by attached to the chromatography resin. This DR15 affinity resin may then be used to bind an TXNL and the bound complex used to identify compounds that compete for binding the TXNL with the active DR15 compound, typically by washing the resin with a candidate compound and determining whether the candidate compound disrupts the TXNL-DR15 compound complex by assaying for the release of TXNL from the resin.

Although candidate compounds may be screened for the ability to bind an TXNL on a compound-by-compound basis, it may be more convenient to screen large numbers of candidate compounds simultaneously using one of the many library screening methodologies known in the art. One art-known approach uses recombinant bacteriophage to produce large libraries of peptides which can then be screened in a variety of formats for binding to a TXNL. Using such phage methods, very large libraries of candidate peptides can be constructed (e.g., $10^6$-$10^8$ peptides) and screened for binding with a TXNL. Methods for constructing and screening such "phage display" libraries are described, for example, in Scott & Smith, 1990, Science 249:386-390; Cwirla et al., 1990, Proc. Natl. Acad. Sci. 87:6378-6382; 1990); Devlin et al., 1990, Science 249:404-406 (1990); U.S. Pat. Nos. 5,427,908; 5,432,018; 5,580,717 and 5,723,286, the disclosures of which are incorporated herein by reference. Other non-limiting examples of recombinant library methodologies that may be used in connection with the assays of the invention are described in U.S. Pat. Nos. 6,156,571; 6,107,059 and 5,733,731, the disclosures of which are incorporated herein by reference.

A second art-known approach uses chemical methods to synthesize libraries of compounds, such as small organic compounds, peptides and/or peptide analogs, attached to beads or wafers that can then be conveniently screened for binding with a TXNL. The libraries may be encoded or non-encoded. Methods of synthesizing such immobilized libraries, as well as methods of screening the libraries are described, for example, in Houghten, 1985, Proc. Natl. Acad. Sci. USA 82:5131-5735; Geysen et al., 1986, Molecular Immunology 23:709-715; Geysen et al., 1987, J. Immunologic Method 102:259-274; Frank & Döring, 1988, Tetrahedron 44:6031-6040; Fodor et al., 1991, Science 251: 767-773; Furka et al., 1988, 4th International Congress of Biochemistry, Volume 5, Abstract FR:013; Furka, 1991, Int. J. Peptide Protein Res. 37:487-493; Frank, 1992, Tetrahedron 48:9217-9232; Needels et al., 1993, Proc. Natl. Acad. Sci. USA 90:10700-10704; DeWitt et al., 1993, Proc. Natl. Acad. Sci. USA 90:6909-6913; Frank et al., 1993, Biorg. Med. Chem. Lett. 3:425-430; Ohlmeyer et al., 1993, Proc. Natl. Acad. Sci. USA 90:10922-10926; WO 92/00252; WO 9428028; U.S. Pat. Nos. 6,329,143; 6,291,183; 5,885,837; 5,424,186; 5,384,261; 6,165,717; 6,143,497; 6,140,493; 5,789,162; 5,770,358; 5,708,153; 5,639,603; 5,541,061; 5,525,735; 5,525,734; 6,261,776; 6,239,273; 5,846,839; 5,770,455; 5,770,157; 5,6019,826; 6,001,579; 5,968,736; 5,962,337; 5,789,172; 5,721,099; 5,565,324; 5,010,175; and 4,631,211, the disclosures of which are incorporated herein by reference. For reviews of some of these techniques, see Ellman et al., 1996, Account, Chem. Res. 29:132-143; Gallop et al., 1994, J. Med. Chem. 37:1233-1251; Gordon et al., 1994, J. Med. Chem. 37:1385-1401. Non-limiting examples of solid-phase chemical synthesis strategies and conditions useful for synthesizing combinatorial libraries of small organic and other compounds may be found in Bunin, 1998, *The Combinatorial Index,* Academic Press, London, England (see, e.g., Chapter 1-5) and Hermkens et al., 1996, Tetrahedron 52:4527-4554, as well as the references cited therein, the disclosures of which are incorporated herein by reference.

Another art-known approach utilizes solution-phase chemical synthesis techniques to synthesize libraries of compounds, such as, for example, libraries of small organic compounds, which may then be screened in the assays of the invention. Methods for synthesizing and screening such solution-phase libraries are well-known and are described, for example, in Bunin, 1998, *The Combinatorial Index,* Academic Press, England (see, e.g., Chapter 6); WO 95/02566; U.S. Pat. Nos. 5,962,736; 5,766,481; 5,736,412 and 5,712,171, and the references cited therein; the disclosures of which are incorporated herein by reference. Additional review articles, references, patents and books describing myriad techniques for synthesizing and screening libraries of compounds for the ability to bind another compound such as a TXNL can be found at Lebl & Leblova: Dynamic Database of References in Molecular Diversity, Internet http://www.5z.com (see especially the diversity information pages at http://www.5z.com/divinfo).

Once a candidate compound that binds the TXNL has been identified, further assays may be carried out to characterize the binding characteristics of the compound, for example, to determine its binding affinity, dissociation constant (Kd), on- and/or off-rates, etc., using well-known techniques. For example, binding affinities can be determined using saturation kinetics and Scatchard analysis. For saturation kinetics, the binding assay can be performed with increasing concentrations of the candidate compound, which is typically labeled with, for example, a radiolabel. Competitive binding experiments with an active DR15 or other active compound, for example peptide DR15wt (SEQ ID NO:1), peptide DR15PE (SEQ ID NO:2), peptide DR15QI (SEQ ID NO:3), or peptide DR15YM (SEQ ID NO:4), can be carried out with increasing concentrations of unlabeled candidate compound and a fixed concentration of labeled (for example radiolabeled) active DR15 or other compound.

An alternative method for characterizing receptor/ligand binding characteristics of a plurality of compounds in parallel that may be adapted for use in connection with the invention is described in U.S. Pat. No. 5,324,633.

In one embodiment of the invention, the candidate compounds identified will have a dissociation constant (Kd) for TXNL on the order of 1 mM, 100 µM, 10 µM, 1 µM, 100 nM, 10 nM, 1 nM or even lower. In another embodiment of the invention, the candidate compounds identified will exhibit an $IC_{50}$ in a competitive binding assay with an active DR15 compound of the invention or another compound that competes for binding an TXNL with an active DR15 compound of the invention on the order of 1 mM, 100 µM, 10 µM, 1 µM, 100 nM, 10 nM, 1 nM or even lower. In this context, the $IC_{50}$ represents the concentration of candidate compound that displaces 50% of the bound DR15 or other compound. Suitable assays for measuring such $IC_{50}$s are well-known.

If desired, the ability of identified candidate compounds to modulate or regulate IL-4 induced IgE production and/or processes associated therewith can be confirmed in in vitro assays, such as those described herein in connection with the identification of the DR15 compounds, for example, as described in the Examples. Other assays that are well known in the art may be used, for example, those described in U.S. Pat. No. 5,958,707.

Knowledge of the interaction surface between a DR15 compound of the invention such as peptide DR15wt (SEQ ID NO:1), peptide DR15PE (SEQ ID NO:2), peptide DR15QI (SEQ ID NO:3) and/or DR15YM (SEQ ID NO:4) and a TXNL, and in particular the TXNL amino acids involved in binding the DR15 compound, can also provide useful information for identifying compounds that bind a TXNL. Identification and screening of TXNL binding compounds is further facilitated by determining structural features of an TXNL-DR15 compound complex, e.g., using X-ray crystallography, neutron diffraction, nuclear magnetic resonance spectrometry or any other techniques for structure determination. These techniques provide for the rational design or in silico identification of compounds that bind a TXNL. The crystal structure of the N-terminus 105 amino-acids of hTXNL has been determined to 1.5A resolution. (Chen et al., 2001, Acta Crystallogr D Biol Crystalogr 57(pt11): 1712-4; NCBI gi|14278250|pdb|1GH2|A [14278250].

Candidate compounds identified using the screening assays of the invention may be agonists or antagonists of the TXNL. Thus, the identified compounds may bind to the TXNL without activating it or may inhibit one or more biological activities of TXNL (antagonist) or, alternatively, the identified compounds may activate one or more biological activities of the TXNL (agonists). These functional assays also provide an indirect means of assessing whether a candidate compound binds a TXNL. Observation of agonist or antagonist activity indicates the candidate compound binds the TXNL. Thus, the method of the invention may employ functional assays of TXNL activity to determine whether a candidate compound binds TXNL. Suitable methods for determining the effect of the candidate compound on the activity of TXNL and fragments thereof include, for example, methods described in Lee et al., 1998, supra.

Kits

The invention also provides kits for carrying out the various screening assays and methods of the invention. Such kits will typically include a TXNL and a compound that competes for binding with the TXNL, such as an active DR15 compound. The TXNL and/or compound may be labeled or unlabeled. The kit may further include additional components useful for carrying out the assays and methods. Non-limiting examples of such additional components include labels, labeling reagents, binding buffers, etc. The kit may also include instructions teaching its methods of use. In one embodiment, the kit comprises and TXNL and a compound selected from peptide DR15wt (SEQ ID NO:1), peptide DR15PE (SEQ ID NO:2), peptide DR15QI (SEQ ID NO:3), or peptide DR15YM (SEQ ID NO:4) and an analog thereof.

Uses of the DR15 Compounds and Identified Compounds

As discussed previously, the active DR15 compounds of the invention and/or the active TXNL-binding compounds identified by the above-described screening methods (referred to collectively as "active compounds"), can be used in a variety of in vitro, in vivo and ex vivo applications to regulate or modulate processes involved with the production and/or accumulation of IgE. For example, the active compounds can be used to modulate, and in particular inhibit, any or all of the following processes in vitro, in vivo or ex vivo: IgE production and/or accumulation; the IL-4 receptor-mediated signaling cascade leading to isotype switching and/or production of IgE; IL-4 induced switching of B-cells to produce IgE, IL-4 mediated IgE production; and IL-4 induced germline ε transcription. In a specific embodiment of the invention, the active compounds may be used to treat or prevent diseases characterized by, caused by or associated with production and/or accumulation of IgE. Such treatments may be administered to animals in veterinary contexts or to humans. Diseases that are characterized by, caused by or associated with IgE production and/or accumulation, and that can therefore be treated or prevented with the active compounds include, by way of example and not limitation, anaphylactic hypersensitivity or allergic reactions and/or symptoms associated with such reactions, allergic rhinitis, allergic conjunctivitis, systemic mastocytosis, hyper IgE syndrome, IgE gammopathies, atopic disorders such as atopic dermatitis, atopic eczema and/or atopic asthma and B-cell lymphoma.

When used to treat or prevent such diseases, the active compounds may be administered singly, as mixtures of one or more active compounds or in mixture or combination with other agents useful for treating such diseases and/or symptoms associated with such diseases. The active compounds may also be administered in mixture or in combination with agents useful to treat other disorders or maladies, such as steroids, membrane stabilizers, 5LO inhibitors, leukotriene synthesis and receptor inhibitors, IgE receptor inhibitors, β-agonists, tryptase inhibitors and antihistamines, to name a few. The active compounds may be administered per se or as pharmaceutical compositions.

Pharmaceutical compositions comprising the active compounds of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically. The actual pharmaceutical composition administered will depend upon the mode of administration. Virtually any mode of administration may be used, including, for example topical, oral, systemic, inhalation, injection, transdermal, etc.

The active compound may be formulated in the pharmaceutical compositions per se, or in the form of a pharmaceutically acceptable salt. As used herein, the expression "pharmaceutically acceptable salt" means those salts which retain substantially the biological effectiveness and properties of the active compound and which is not biologically or otherwise undesirable. Such salts may be prepared from inorganic and organic acids and bases, as is well-known in the art. Typically, such salts are more soluble in aqueous solutions than the corresponding free acids and bases.

For topical administration, the active compound(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For administration by inhalation, the active compound(s) can be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For prolonged delivery, the active compound(s) can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives; e.g., as a sparingly soluble salt.

Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compounds(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

Gene Therapy

As will be recognized by skilled artisans, active compound(s) that are peptides composed wholly of genetically-encoded amino acids may be administered utilizing well-known gene therapy techniques. According to such techniques, a gene encoding the active compound may be introduced either in vivo, ex vivo, or in vitro in a viral vector. Such vectors include an attenuated or defective DNA virus, such as but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred.

Defective virus is not infective after introduction into a cell. Use of defective viral vectors allows for administration to cells in a specific, localized area, without concern that the vector can infect other cells. For example, in the treatment of the various diseases described herein, lymphocyte B-cells can be specifically targeted. Examples of particular vectors include, but are not limited to, a defective herpes virus I (HSV1) vector (Kaplitt et al., 1991, Molec. Cell. Neurosci.

2:320-330), an attenuated adenovirus vector, such as the vector described by Stratford-Perticaudet et al., 1992, J. Clin. Invest. 90:626-630 and a defective adeno-associated virus vector (Samulski et al., 1987, J. Virol. 61:3096-3101; Samulski et al., 1989, J. Virol. 63:3822-3828).

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, 1995, Nat. Med. 1(9):887-889). In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120 (1988); Temin et al., U.S. Pat. No. 5,124,263; Dougherty et al., WO 95/07358; and Kuo et al., 1993, Blood 82:845. Targeted gene delivery is described in WO 95/28494.

Alternatively, the vector can be introduced by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., 1987, Proc. Natl. Acad. Sci. USA 84:7413-7417; Mackey et al., 1988, Proc. Natl. Acad. Sci. USA 85:8027-8031). The use of cationic lipids may promote encapsulation of negatively charged nucleic acids, and also promote fusion with negatively charged cell membranes (Felgner & Ringold, 1989, Science 337:387-388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting (see Mackey et al., 1988, supra). Targeted peptides, e.g., hormones or neurotransmitters, and proteins such as antibodies, or non-peptide molecules could be coupled to liposomes chemically.

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., 1992, J. Biol. Chem. 267:963-967; Wu & Wu, 1988, J. Biol. Chem., 263:14621-14624; Canadian Pat. Application No.2,012,311).

Naked nucleic acids encoding the active compound may also be introduced using the gene-activated matrices described, for example, in U.S. Pat. No. 5,962,427.

Effective Dosages

The active compound(s) of the invention, or compositions thereof, will generally be used in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated, e.g., eradication or amelioration of the underlying allergy, atopic dermatitis, atopic eczema or atopic asthma, and/or eradication or amelioration of one or more of the symptoms associated with the underlying disorder such that the patient reports an improvement in feeling or condition, notwithstanding that the patient may still be afflicted with the underlying disorder. For example, administration of an active compound to a patient suffering from an allergy provides therapeutic benefit not only when the underlying allergic response is eradicated or ameliorated, but also when the patient reports a decrease in the severity or duration of the symptoms associated with the allergy following exposure to the allergen. Therapeutic benefit also includes halting or slowing the progression of the disease, regardless of whether improvement is realized.

For prophylactic administration, the active compound may be administered to a patient at risk of developing a disorder characterized by, caused by or associated with IgE production and/or accumulation, such as the various disorders previously described. For example, if it is unknown whether a patient is allergic to a particular drug, the active compound may be administered prior to administration of the drug to avoid or ameliorate an allergic response to the drug. Alternatively, prophylactic administration may be applied to avoid the onset of symptoms in a patient diagnosed with the underlying disorder. For example, an active compound may be administered to an allergy sufferer prior to expected exposure to the allergen. Active compounds may also be administered prophylactically to healthy individuals who are repeatedly exposed to agents known to induce an IgE-related malady to prevent the onset of the disorder. For example, an active compound may be administered to a healthy individual who is repeatedly exposed to an allergen known to induce allergies, such as latex allergy, in an effort to prevent the individual from developing an allergy.

The amount of active compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Initial dosages may be estimated initially from in vitro assays. For example, an initial dosage for use in animals may be formulated to achieve a circulating blood or serum concentration of active compound that inhibits about 25% or more of IL-4 induced IgE production, or a process associated therewith, such as germline ε transcription, as measured in an in vitro assay. Alternatively, an initial dosage for use in animals may be formulated to achieve a circulating blood or serum concentration of active compound that is equal to or greater than the $IC_{50}$ as measured in a TXNL competitive binding assay with an active DR15wt compound of the invention, such as peptideDR15wt (SEQ ID NO:1), peptide DR15PE (SEQ ID NO:2), peptide DR15QI (SEQ ID NO:3), orpeptide DR15YM (SEQ ID NO:4). Calculating dosages to achieve such circulating blood or serum concentrations taking into account the bioavailability of the particular active compound is well within the capabilities of skilled artisans. For guidance, the reader is referred to Fingl & Woodbury, "General Principles," In: *The Pharmaceutical Basis of Therapeutics,* Chapter 1, pp. 1-46, 1975, and the references cited therein.

Initial dosages can also be estimated from in vivo data, such as animal models. Animals models useful for testing the efficacy of compounds to treat or prevent diseases characterized by, caused by or associated with IgE production and/or accumulation are well-known in the art. Suitable animal models of hypersensitivity or allergic reactions are described in Foster, 1995, Allergy 50(21Suppl):6-9, discussion 34-38 and Tumas et al., 2001, J. Allergy Clin. Immunol. 107(6):1025-1033. Suitable animal models of allergic rhinitis are described in Szelenyi et al., 2000, Arzneimittelforschung 50(11):1037-42; Kawaguchi et al., 1994, Clin. Exp. Allergy 24(3):238-244 and Sugimoto et al., 2000, Immunopharmacology 48(1):1-7. Suitable animal models of allergic conjunctivitis are described in Carreras et al., 1993, Br. J. Ophthalmol. 77(8):509-514; Saiga et al., 1992, Ophthalmic Res. 24(1):45-50; and Kunert et al., 2001 Invest. Ophthalmol. Vis. Sci. 42(11):2483-2489. Suitable animal modules of systemic mastocytosis are described in O'Keefe et al., 1987, J. Vet. Intern. Med. 1(2):75-80 and Bean-Knudsen et al., 1989, Vet. Pathol. 26(1):90-92. Suitable animal models of hyper IgE syndrome are described in Claman et al., 1990, Clin. Immunol. Immunopathol. 56(1):46-53. Suitable animal models of B-cell lymphoma are described in Hough et al., 1998, Proc. Natl. Acad. Sci. USA 95:13853-13858 and Hakim et al., 1996, J. Immunol. 157(12):5503-5511. Suitable animal models of atopic disorders such as atopic dermatitis, atopic eczema and atopic asthma are described in Chan et al., 2001, J. Invest. Dermatol. 117(4):977-983 and Suto et al., 1999, Int. Arch. Allergy Immunol. 120(Suppl 1):70-75. Ordinarily skilled artisans can routinely adapt such information to determine dosages suitable for human administration.

Dosage amounts will typically be in the range of from about 1 mg/kg/day to about 100 mg/kg/day, 200 mg/kg/day, 300 mg/kg/day, 400 mg/kg/day or 500 mg/kg/day, but may be higher or lower, depending upon, among other factors, the activity of the active compound, its bioavailability, the mode of administration and various factors discussed above. Dosage amount and interval may be adjusted individually to provide plasma levels of the active compound(s) which are sufficient to maintain therapeutic or prophylactic effect. In cases of local administration or selective uptake, such as local topical administration, the effective local concentration of active compound(s) may not be related to plasma concentration. Skilled artisans will be able to optimize effective local dosages without undue experimentation.

The compound(s) may be administered once per day, a few or several times per day, or even multiple times per day, depending upon, among other things, the indication being treated and the judgement of the prescribing physician.

Preferably, the active compound(s) will provide therapeutic or prophylactic benefit without causing substantial toxicity. Toxicity of the active compound(s) may be determined using standard pharmaceutical procedures. The dose ratio between toxic and therapeutic (or prophylactic) effect is the therapeutic index. Active compound(s) that exhibit high therapeutic indices are preferred.

The invention having been described, the following examples are offered by way of illustration and not limitation.

EXAMPLES

Identification of Peptide DR15wt from a Random Library of Peptide 20-mers

Peptide DR15wt (SEQ ID NO:1) was identified by screening a retroviral library of random peptide 20-mers for the ability to inhibit IL-4 induced germline $\epsilon$ transcription using the HBEGF2a/diphtheria dual reporter phenotypic screening system described in WO 01/31232. To construct the random library, A5T4 reporter cells (described in more detail below) were infected with an infectious retroviral library of random peptide 20-mers (prepared as described in WO 97/27213; see also WO 01/34806 at page 39, line 36 through page 40, line 19). The retroviral vector used includes a gene encoding blue fluorescent protein (BFP) fused upstream of the region encoding the random peptide via a linker region encoding an α-helical peptide linker (expression fusion product is referred to as "BFP-peptide"). Expression of the BFP-peptide product is controlled by a promoter sensitive to the tetracycline-regulated transactivator such that expression of the BFP-peptide is regulated by tetracycline (Tet) or doxycycline (Dox). See U.S. patent application Ser. No. 10/096,339, entitled "Methods and Compositions for Screening for Altered Cellular Phenotypes", filed on Mar. 8, 2002. The BFP reporter gene provides a rapid phenotypic assay to determine whether cells were infected: infected cells express BFP-peptide and fluoresce blue (phenotype BFP$^+$), uninfected cells do not express BFP-peptide, and do not fluoresce blue (phenotype BFP$^-$). To reduce the number of stop codons, the region of the vector encoding the random peptide was of the sequence (NNK)$_{20}$, where each N independently represents A, T, C or G and K represents T or G. The library was also biased to account for degeneracy in the genetic code.

The A5T4 reporter cell line was engineered from BJAB B-cells (Menezes et al., 1975, Biomedicine 22:276-284; Source: Yoshinobu Matsuo, PhD., Fujisaki Cell Center, Hayashibara Biochemical Labs, Inc., 675-1 Fujisaki, Okayama 702-8006, Japan) and includes a reporter gene encoding the HBEGF2a/GFP dual function reporter positioned downstream of an engineered 603 base pair IL-4 responsive fragment of an $\epsilon$ promoter (FIG. 1; see also WO 99/58663) such that ultimate expression of the dual function reporter is driven by the $\epsilon$ promoter. When expressed, the dual function reporter cleaves into two pieces, a heparin-binding epidermal growth factor-like growth factor (HBEGF) and a green fluorescent protein (GFP), via the self-cleaving 2a sequence (Donnelly et al., 2001, J. Gen. Viol. 82:1027-1041; Donnelly et al., 1997, J. Gen. Virol. 78:13-21; Mattion et al., 1996, J. Virol. 70:8124; Ryan et al., 1994, EMBO J 13:928-33 Ryan et al., 1991, J. Gen. Virol. 72:2727; Hellen et al., 1989, Biochem. 28:9881; see also, WO 99/58663). In this reporter system, cells ectopically expressing HBEGF are capable of translocating diphtheria toxin (DT) into their cytoplasm, leading to rapid, acute cytotoxicity. Cells that do not express HBEGF are spared this fate and continue to survive even in the presence of high concentrations of DT. The A5T4 reporter cell line was further engineered to express the tetracycline-regulated transactivator (tTA), allowing for regulation of peptide library expression with tetracycline (Tet) or doxycycline (Dox). See U.S. patent application Ser. No. 10/096,339 the disclosure of which is incorporated herein by reference. Thus, according to this dual phenotypic reporter system, unstimulated control cells expressing a random peptide fluoresce blue (BFP$^+$) in the absence of Tet or Dox. In the presence of Tet or Dox, the peptide is not made and the cells are BFP$^-$. Following stimulation with IL-4, BFP$^+$ cells expressing a non-inhibitory peptide fluoresce green and, in addition, are sensitive to DT. Stimulated BFP$^+$ cells expressing an inhibitory peptide do not fluoresce green and are not DT sensitive. The toxin-conditional selection and Tet or Dox-controlled peptide expression features of the A5T4 screening line are illustrated in FIGS. 2A & 2B, respectively.

Following infection, the library was enriched for cells expressing peptides that inhibit IL-4 induced ε transcription as generally outlined in the top half of FIG. 3 and sorted by FACS into single cell clones. The clones were then screened as generally illustrated in the lower half of FIG. 3. Briefly, for screening, each clone was divided into two populations and one population was treated with Dox (10 ng/ml). After 5 days, both populations were stimulated with IL-4 (final conc. 60 U/mL; PeptroTech, Inc.) and, after 3 more days, both populations were analyzed by FACS to measure BFP and GFP fluorescence. FACS data were converted to a "reporter ratio", which is defined for this purpose as the ratio of the geometric mean of GFP fluorescence of the +IL-4/+Dox to the +IL-4/−Dox populations. Cells expressing a peptide that inhibits germline ε transcription have a reporter ratio of ≧1.1. A reporter ratio of ≧1.2 is indicative of strong inhibition.

The sequences of peptides expressed by positive clones (reporter ratios of ≧1.1) were obtained by RT-PCR amplification of the integrated peptide-expressing sequences. In this experiment, of $2.4 \times 10^9$ A5T4 cells infected, 218 positive clones were identified, 199 of which were unique. From this same experiment, 155 total clones with a reporter ratio of ≧1.19 were identified, 136 of which were unique. Clone DR15, which encodes peptide DR15wt, was amongst the positive clones identified (clone DR15 had a reporter ratio of 1.43).

Clone DR15 Transfers its Phenotype Into Naïve Cells

Figure 4:
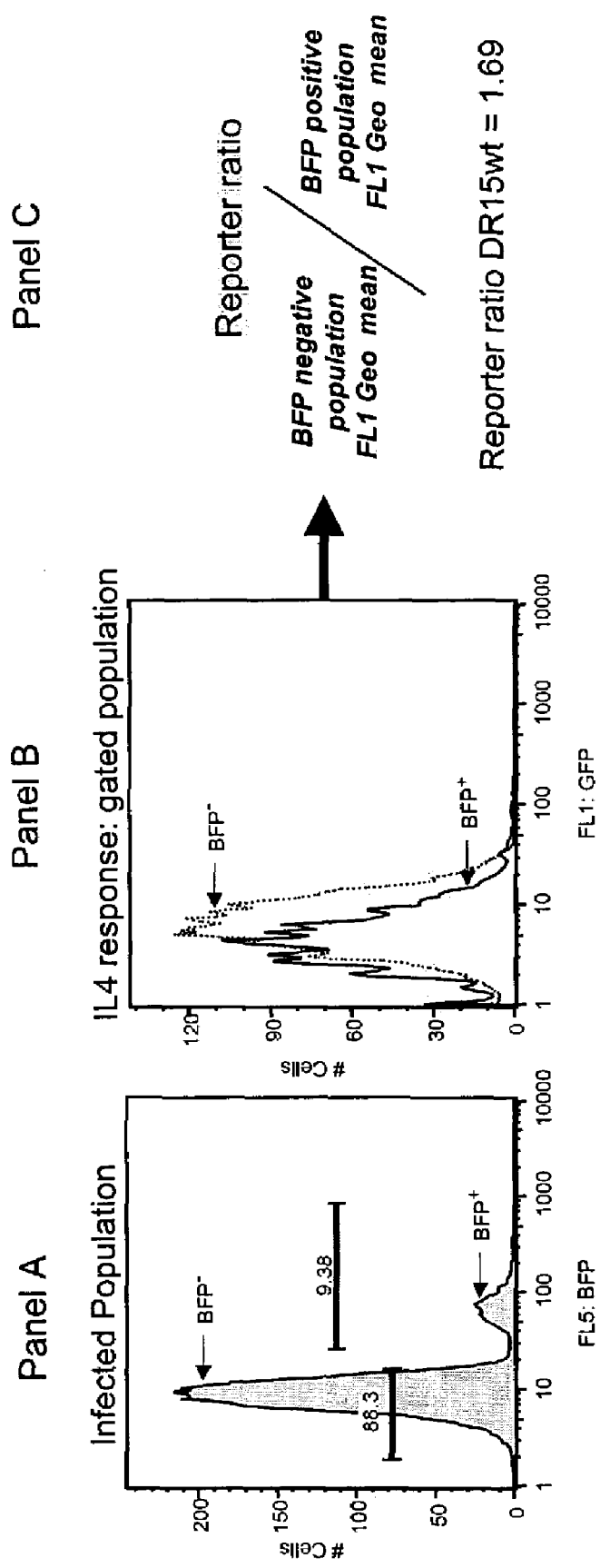
FIG. 4 provides DNA transfer data for peptide DR15wt.

The ability of peptide DR15wt (SEQ ID NO:1) to inhibit germline ε transcription was confirmed in naïve cells. Briefly, Phoenix cells were transfected with a retroviral vector encoding a BFP-DR15wt (SEQ ID NO:1) peptide fusion as described in WO 99/58663 and WO 97/27213. Naïve A5T4 cells were infected with the resultant virions and grown for 3 days. The infected cells were stimulated with IL-4 (60 U/mL) and, after 3 days, the cells were assessed by FACS for BFP and GFP. The FACS data are presented in FIG. 4. As illustrated in FIG. 4, there are two populations of cells: infected cells that express the BFP-peptide fusion (BFP+) and uninfected cells that do not (BFP−). The BFP fluorescence data corresponding to the BFP+ and BFP− populations are provided in Panel A. The GFP fluorescence data corresponding to the BFP+ and BFP− populations are presented in Panel B. The reporter ratio for this purpose is determined as the geometric mean of the GFP fluorescence of the BFP− population divided by the geometric mean of the GFP fluorescence of the BFP+ population. The reporter ratio for the DR15 in this re-infection assay was 1.69.

Peptide DR15wt Inhibits Transcription of an Endogenous Germline ε Promoter

The ability of peptide DR15wt (SEQ ID NO:1) to inhibit transcription of an endogenous germline ε promoter was confirmed using a TAQMAN® assay (Roche Molecular, Alameda, Calif.). Briefly, A5T4 cells were infected with retrovirus capable of expressing peptide DR15wt (SEQ ID NO:1) (prepared as described above). The cells were sorted for BFP+ to select for infected cells. Infected cells were divided into two populations. One population was exposed to Dox (10 ng/ml). Both populations were stimulated with IL-4 (60 U/ml). After 3 days, the cells were pelleted and the pellets assayed for ε promoter transcription using a TAQMAN assay performed as described in Applied Biosystems Protocol 4310299 (available at http:\\www.appliedbiosystems.com). The primers and probe, which are specific for the transcription product driven by the A5T4 endogenous ε promoter, were as follows (the probe was labeled at the 5'-end with Fam and at the 3'-end with Tamra):

```
ε forward primer:
ATCCACAGGCACCAAATGGA      (SEQ ID NO:7)

ε reverse primer:
GGAAGACGGATGGGCTCTG       (SEQ ID NO:8)

ε probe:
ACCCGGCGCTTCAGCCTCCA      (SEQ ID NO:9)
```

The measured endogenous ε inhibition ratio, defined as the ratio of the relative expression units (TAQMAN quantitative PCR of ε transcription product) of +IL-4/+Dox to +IL-4/−Dox cells, was 1.56 (average of 3 values; p=0.0023), indicating that peptide DR15wt (SEQ ID NO:1) strongly inhibits the endogenous germline ε promoter.

Peptide DR15wt is Selective for the Germline ε Promoter

To demonstrate selectivity for the germline ε promoter, peptide DR15wt (SEQ ID NO:1) was tested for inhibition of germline α transcription. The assay was similar to that described in the immediately preceding section, except that ST486 cells (ATCC #CRL-1647) engineered to express the tetracycline-regulated transactivator were infected and the infected cells were stimulated with TGF-β (40 ng/ml; Peprotech). The primers and probe, which are specific for the transcription product driven by the ST486 endogenous α promoter, were as follows (the probe was labeled at the 5'-end with Fam and at the 3'-end with Tamra):

```
α forward primer:
CAGCACTGCGGGCCC           (SEQ ID NO:10)

α reverse primer:
TCAGCGGGAAGACCTTGG        (SEQ ID NO:11)

α probe:
CCAGCAGCCTGACCAGCATCCC    (SEQ ID NO:12)
```

The measured endogenous α inhibition ratio was 0.98 (average of 3 values; p=0.7797), indicating that peptide DR15wt (SEQ ID NO: 1) does not inhibit transcription of the germline α promoter. These data confirm that peptide DR15wt (SEQ ID NO:1) is a selective inhibitor of germline ε transcription.

IgE Synthesis and ELISA Assay

This example describes an IgE synthesis mixed lymphocyte and ELISA assay that may be used to assess the amount of IgE produced by cells such as human peripheral blood lymphocytes or other lymphatic cells in the presence and absence of candidate compounds, such as DR15 compounds and/or compounds identified in the screening assays of the invention.

IgE Synthesis Assay (a) Materials

In the various protocols that follow below, the following materials are used:

Heparin (Sigma H3393, St. Louis, Mo.)

Histopaque 1077 tubes (Sigma A0561, St. Louis, Mo.)

Iscove's Modified Dulbeccos Medium ("IMDM); Sigma I3390, St. Louis, Mo.)

Bovine Serum Albumin ("BSA"; Sigma A9418, St. Louis, Mo.).

Fetal Bovine Serum ("FCS"; Sigma F7524, St. Louis, Mo.). (the serum is heat inactivated prior to use at 56° C. for 30 minutes, aliquoted and stored at −20° C.; "HI-FCS")

Human Transferrin (Sigma T2252, St. Louis, Mo.)

Bovine Insulin (Sigma I1882, St. Louis, Mo.)

200 mM L-Glutamine ("L-Gln") Sigma G7513, St. Louis, Mo.) (stored as 5 ml aliquots at −20° C.)

Pen/Strep 10% solution (Sigma P0781, St. Louis, Mo.) (stored as 5 ml aliquots at −20° C.)

PBS Dulbeccos (Gibco BRL 14190-094, now Invitrogen, Carlsbad, Calif.)

DMSO (Sigma D2650, St. Louis, Mo.)

Recombinant Human IL-4 (R&D Systems 204-1L, Minneapolis, Minn.) (stored as a stock solution of 100,000 U/ml in culture medium at −20° C.)

96 well tissue culture plates (Costar 3595, Corning Inc., Life Sciences, Acton Mass.)

96 well dilution blocks (Porvair 219008, Shepperton, UK)

Culture Medium: supplement 500 ml IMDM with 0.5% BSA (2.5 g), 10% HI-FCS (50 ml), 25 mg human transferrin, 2.5 mg bovine insulin, 2 mM L-Gln (5 ml) and 1% pen/strep (5 mL). Filter sterilize before use.

(b) Blood Collection

Make up a 1 mg/ml solution of heparin in sterile PBS and place 1 ml in each sterile 50 ml centrifuge tube required. Collect 50 ml of venous blood from a healthy human volunteer per centrifuge tube.

(c) Lymphocyte Isolation

Lymphocytes are isolated from the blood according to the protocol below:

1. Dilute blood with an equal volume of PBS containing 2% HI-FCS.
2. Add 20 ml diluted blood to each histopaque tube. The histopaque tubes should be warmed to room temperature before use. They can be left overnight at room temp in the dark and then spun at 1000 rpm for 5 min to settle the contents before use. Spin at 1000 g for 35 min at room temperature in a benchtop centrifuge with the break set to off.
3. Draw off the upper plasma layer and discard.
4. Draw off the lymphocyte layer into a sterile centrifuge tube. If there is clear definition between the bottom of the lymphocyte layer and the top of the frit, remove only the lymphocyte layer, not all the liquid above the frit.
5. Add 30 ml PBS-2% HI-FCS to each 10 ml of cell suspension and spin at 1000 rpm for 10 min at room temp.
6. Discard the supernatant and resuspend each cell pellet in 5-10 ml PBS-2% HI-FCS. Transfer the suspensions to a single tube and bring the volume to 40 ml with PBS-2% HI-FCS. Spin at 1000 rpm for 10 min at room temp.
7. Repeat Step 6.
8. Wash the cells once with 40 ml culture medium.
9. Discard the supernatant and resuspend the pellet in 10 ml or less culture medium.
10. Count the cells (using a Neubauer haemocytometer, a Coulter Max-M cell counter or other counter).
11. Resuspend the cells in culture medium to a concentration of $2 \times 10^6$ cells/ml. The cells can be left at this stage until they are needed for assay set up.

(d) Assay Set Up

The assay is carried out as follows:

1. Dissolve test compounds in DMSO to give a 10 mM stock solution. If necessary, sonicate the stock solution to aid dissolution of the compound.
2. Dilute each compound stock solution 1:20 with culture medium to yield a 500 µM solution in 5% DMSO. Serially dilute this 500 µM stock solution 1:10 with culture medium several times to provide enough stock solutions to test the compounds over a range of concentrations (e.g., from 1 nM to 10 µM).
3. Just prior to use, prepare a stock solution of IL-4 (1000 U/ml in culture medium).
4. To test the compounds and prepare appropriate controls, add to the appropriate wells of a multiwell plate the following reagents in the following amounts:

| Reagent | +IL-4 control | −IL-4 control | Sample |
|---|---|---|---|
| Test Compound | — | — | 50 µl |
| IL-4 | 50 µl | — | 50 µl |
| Culture Medium | — | 50 µl | — |
| 0.5% DMSO in Culture Medium | 50 µl | 50 µl | — |
| Cells | 150 µl | 150 µl | 150 µl |
| Total Volume | 250 µl | 250 µl | 250 µl |

5. Incubate the plates for 10-12 days at 37° C. in a $CO_2$ incubator (5% $CO_2$/95% $O_2$). Following incubation, spin the plates at 1000 rpm for 10 min and store at −20° C. until ready for the ELISA detection assay that follows below.

ELISA Assay for Detection of IgE (a) Materials

In the assay protocol that follows below, the following materials are used:

Nunc maxisorp ELISA plates (GIBCO BRL, now Invitrogen, Carlsbad, Calif.)

Murine anti human IgE (GE1 clone) (Sigma, St. Louis, Mo.)

Phosphate buffered saline ("PBS"; Sigma. St. Louis, Mo.)

Bovine serum albumin ("BSA"; Sigma, St. Louis, Mo.)

Polyethylenesorbitan monolaurate ("TWEEN 20"; Sigma, St. Louis, Mo.)

OPD tablets (DAKO Corp., Carpenteria, Calif.)

Streptavidin biotinylated horseradish peroxidase complex ("Streptavidin HRP"; Amersham, Piscataway, N.J.)

Human Myeloma protein IgE (The Binding Site, Inc.; San Diego, Calif.)

Biotinylated anti human IgE (Vector Laboratories, Inc., Burlingame, Calif.)

Hydrogen peroxide (Sigma, St. Louis, Mo.)

Distilled water ("$dH_2O$")

Buffer A: 0.1 M $NaHCO_3$, pH 9.6

Buffer B: 0.1% TWEEN 20 in PBS

Buffer C: 1% BSA in Buffer B

Stop Solution: 0.6M $H_2SO_4$ (a) Protocol

The assay which measures the amount of IgE synthesized by the various controls and samples prepared above, is carried out as described in the following protocol:

1) Coat Nunc maxisorp plates with 50 µl of murine anti human IgE (1:2000 in Buffer A). Leave plates at 4° C. overnight. Plates can be stored in this way for a maximum of 7 days.
2) Wash plates 3× with Buffer.
3) Block any unbound sites on the plate by adding 200 µl of buffer C. Incubate the plates for at least 2 hours at room temperature. If blocking overnight incubate at 4 C. Blocked plates should only be kept for a maximum of 2 days.

4) Wash plates 3× with Buffer B.
5) Place 50 μl of the sample or standard IgE diluted in Buffer C to each well. IgE standards are diluted to give a concentration range of 100 ng/ml-0 ng/ml. To make up the 100 ng/ml standard, carry out the following dilutions of stock IgE (0.5 mg/ml) in buffer C: 1 in 50 to give a 10 μg/ml solution (a minimum of 10 μls must be transferred from the stock) followed by a 1 in 10 to give 1 μg/ml and then a further 1 in 10 to give 100 ng/ml. Double dilutions are then carried out in buffer C to give the rest of the standard curve. Carry out all dilutions in glass bottles (10 oz) and make up at least 1 ml of each so that reasonable volumes are being transferred (one ELISA plate requires 100 μls of each standard). For the pilot ELISA the standard curve is added to each plate just after the samples have been added. Set up one ELISA plate with 3-4 columns of standards only. This will be used to determine development time at protocol Step 11.

For the pilot ELISA incubate the plates for one-two hours at room temperature

For the full ELISA incubate the plates overnight at 4° C.
6) Wash plates 3× with Buffer B.
7) Add 50 μl of biotinylated anti human IgE (1/500 dilution in Buffer B) to all wells. Incubate the plate for 1 hour at room temperature.
8) Wash plates 3× with Buffer B
9) Add 50 μl of streptavidin HRP to each well (1/800 dilution in Buffer B). Incubate the plates for 45 mins to 1 hour at room temperature. The plates must not be left for longer than 1 hour at this stage.
10) Wash plates 3× with Buffer B.
11) Add 50 μl of substrate (4 OPD tablets per 12 ml dH$_2$O plus 5 μl hydrogen peroxide per 12 ml) to each well and wait for the color to develop (this usually occurs within 10 minutes). Determine the time taken to give the required OD (1.5-2 for 100 ng/ml of standard IgE) using a plate containing only a standard curve. Develop all test plates for this amount of time and in batches of 5 plates. This is especially important if there are a large number of plates.
12) Quench the reaction by adding 50 μl Stop Solution.

Read plates at 492 nm within 30 minutes of stopping the reaction.

Peptide DR15wt Mediates its Inhibitory Action by Binding TXNL

Identification of Potential Binding Partners for Peptide DR15wt

Figure 5A:
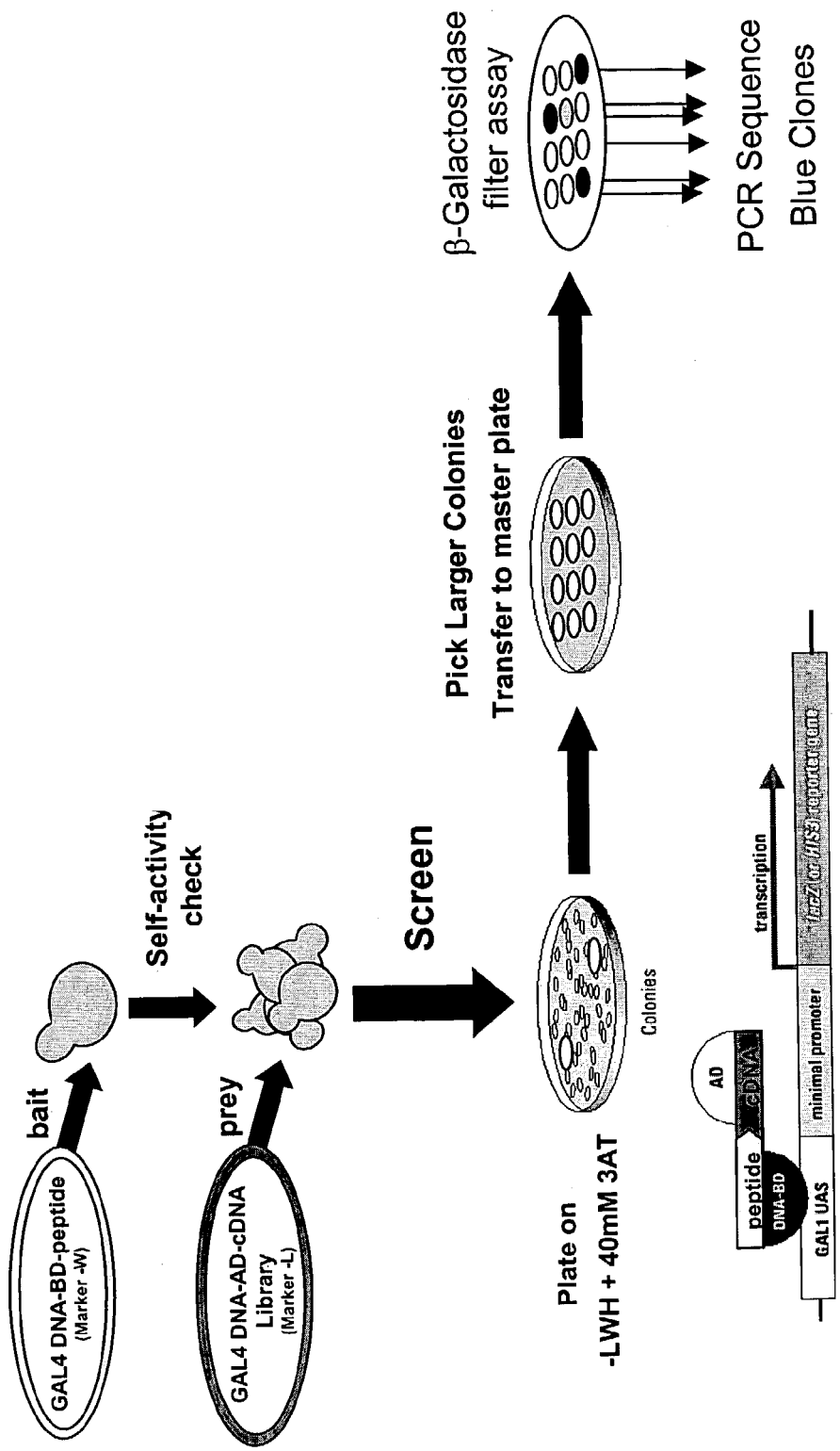
FIG. 5A provides a cartoon outlining a yeast two hybrid (YTH) screening assay used to identify potential binding partners or targets for peptide DR15wt.

Potential binding partners for peptide DR15wt were identified in a β-galactosidase yeast two-hybrid (YTH) assay using peptide DR15wt as bait and a cDNA library constructed from the A5T4 reporter cell line as prey. Binding was assessed by β-galactosidase quantification using BetaFluor (Novagen) as a substrate. A negative interaction control (no cDNA fused downstream of the GAL4 activation domain sequence) was also run. A general outline of the YTH assay is illustrated in FIG. 5A. Following clustering, filtering to remove non-specific bait hits (e.g., GFP and BFP), singletons and clusters recognized by 10 or more cDNA baits (based upon historical YTH assays), and prioritization, 10 prey clones were identified as hits.

Figure 6:
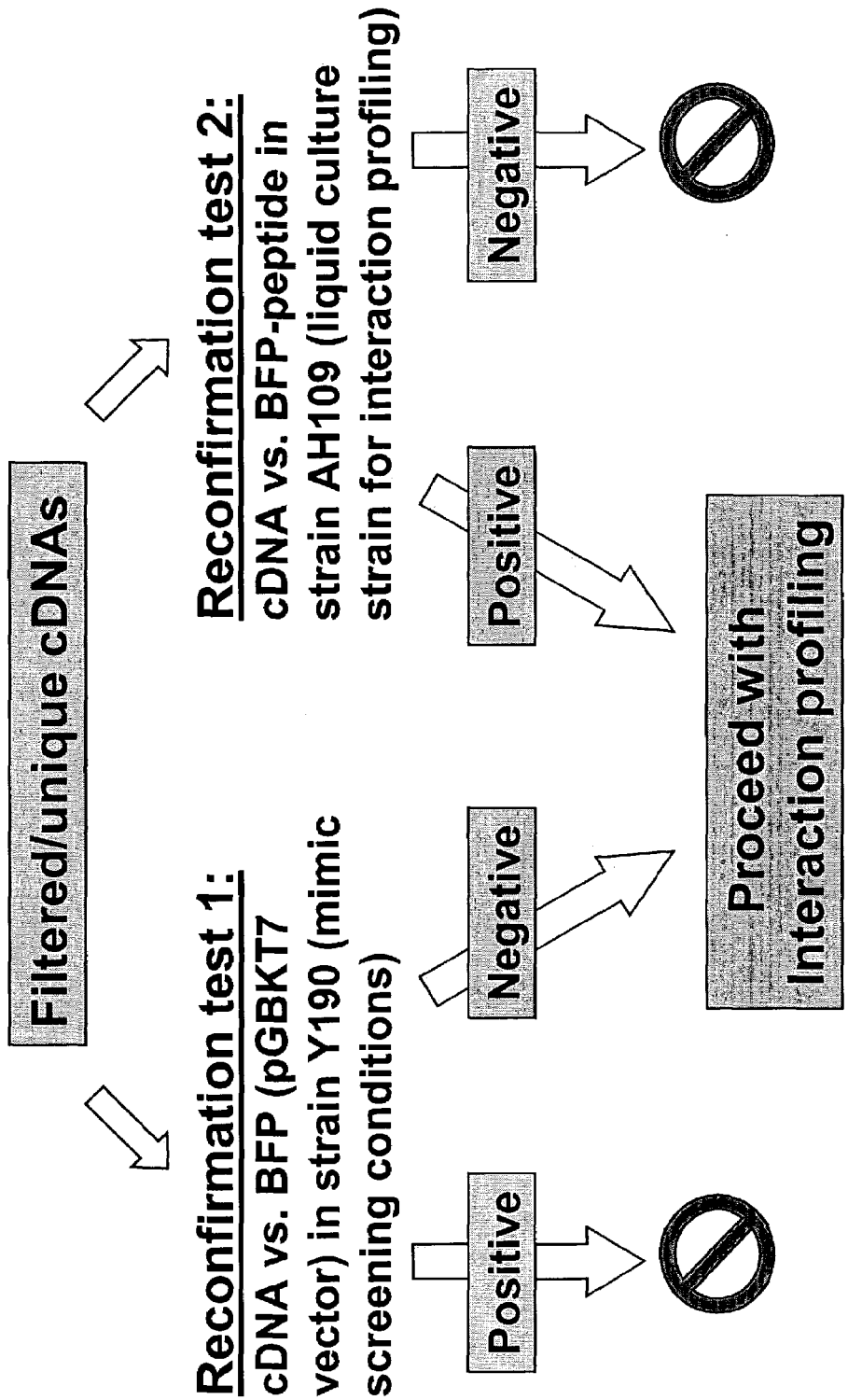
Figure 7:
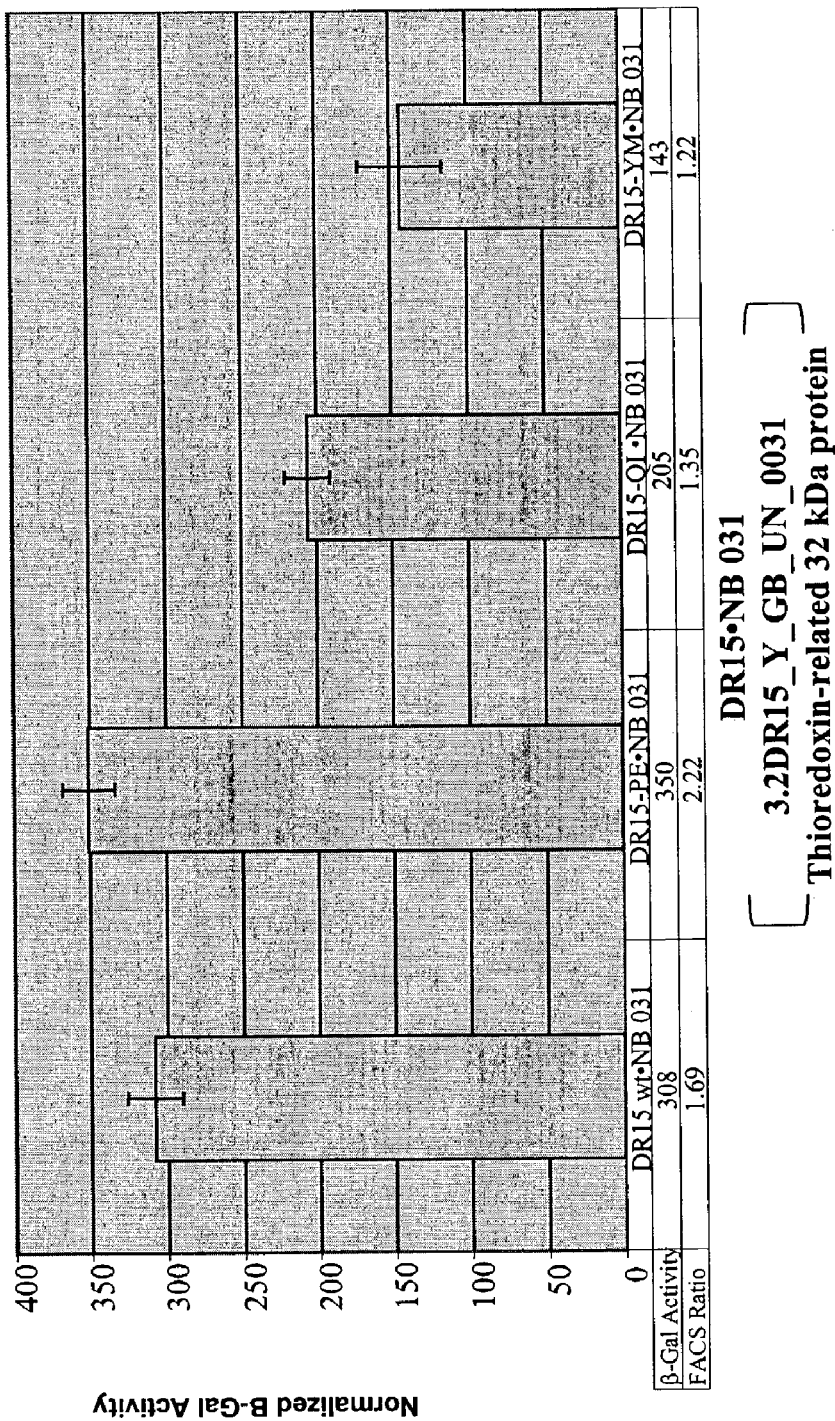

Potential targets identified in the YTH assay were reconfirmed as generally outlined in FIG. 6. The cDNA clones identified as hits in the YTH assay were purified and rescreened for interaction with the DR15wt (SEQ ID NO:1) peptide in a YTH assay. The hit clones were also screened in a control assay for interaction with the BFP using a vector (pGBKT7) that contained only the BFP and not the DR15 peptide. At this stage, 8 putative target clones remained.

In order to further discriminate among the putative targets, functional/interaction profile analyses were carried out as described in copending application Ser. No. 10/095,659, entitled Methods of Identifying Protein Targets, filed Mar. 8, 2002.

Confirmation that Peptide DR15wt Mediates its Inhibitory Action by Binding TXNL

Confirmation of colony 3.2DR15_Y_GB_UN_0031 as the binding partner for peptide DR15wt (SEQ ID NO:1) was confirmed using the profiling method described in copending application Ser. No. 10/095,659 the disclosure of which is incorporated herein by reference. The functional profile was obtained using the A5T4 reporter cell line and the interaction profiles were obtained using the YTH assay and compared for correspondence. The main concept underlying this profiling method is that mutants will tend to act the same way in both the functional assay and an interaction assay with the target polypeptide of the wild-type peptide. That is, a mutant that exhibits an increase in function (as compared to the wild-type peptide) in the functional assay will exhibit an increase in interaction (as compared to the wild-type peptide) in a YTH assay with the target polypeptide of the wild-type peptide. Stated another way, the target polypeptide will yield an interaction profile that corresponds closely to the functional profile when compared visually or by other means.

A collection of DR15 mutants was generated by replacing double amino acid residues in the sequence of DR15wt (SEQ ID NO:1) with a different amino acid, typically an alanine, as described in copending application Ser. No. 10/095,659. The functional profiles for the mutants derived from DR15wt (SEQ ID NO:1) was obtained by constructing and screening for activity in the A5T4 reporter cell line in the manner described above. The activity of each mutant at the germline ε promoter is reflected in the reporter ratio as described above. The reporter ratios were the functional values that were used to develop the functional profiles.

TABLE 2 depicts the amino acid sequences (the dual alanine mutations are underlined) of the mutants tested and the measured reporter ratios when screening in the A5T4 reporter line.

TABLE 2

| Peptide Name | Peptide Sequence | Reporter Ratio | SEQ ID NO |
|---|---|---|---|
| DR15wt | PERCYMRMPPQSLADAQIYS | 1.69 | (SEQ ID NO: 1) |
| DR15PE | AARCYMRMPPQSLADAQIYS | 2.22 | (SEQ ID NO: 2) |
| DR15QI | PERCYMRMPPQSLADAAAYS | 1.35 | (SEQ ID NO: 3) |
| DR15YM | PERCAARMPPQSLADAQIYS | 1.22 | (SEQ ID NO: 4) |

The interaction of DR15wt (SEQ ID NO:1) peptide and its mutants with the clones identified as potential targets for the peptide DR15wt (SEQ ID NO:1) was then quantified in β-galactosidase YTH assay. The YTH assay was performed in the manner described above. A general outline of this YTH assay is illustrated in FIG. 5B. For each clone tested, an interaction profile was developed by comparing the β-galactosidase activity of each mutant to that of the wild type peptide as described above.

Comparison of the interaction and functional profiles was performed by categorizing the mutants of DR15 based on the functional and interaction assays. Based on the reporter ratio each mutant was categorized into one of four functional categories: (1) reduction of function (ROF); (2) loss of function (LOF); (3) increase of function (IOF) or (4) functionally neutral (N) as compared to the activity of the wild type peptide, here DR15wt (SEQ ID NO:1). As mentioned previously, cells expressing a peptide that inhibits germline ε transcription have reporter ratios of ≧1.1. Cells expressing a loss of function (LOF) mutant have a reporter ratio of <1.11. An increase of function mutant (IOF) shows a >50% increase in reporter ratio and a reduction of function (ROF) mutant shows a >50% decrease in reporter ratio. Functionally neutral mutants have reporter ratios that fall within ±50% of that of the DR15wt (SEQ ID NO:1). Using these criteria, peptide DR15QI (SEQ ID NO:3) and peptide DR15YM (SEQ ID NO:4) were designated as ROF mutants, and peptide DR15PE (SEQ ID NO:2) was designated as a IOF mutant. No LOF mutant were found for the DR15 clone.

The interaction of these IOF and ROF mutants with different polypeptides encoded by the putative target clones were quantified using the YTH assay described above. Based on the YTH assay, for each putative target, a subset of the mutants representing each of the above functional categories, when available, were categorized into the following four interaction categories: (1) reduction of interaction (ROI); (2) loss of interaction (LOI); (3) increase of interaction (IOI); and (4) interactionally neutral (N), by assessing the binding affinity ratio of the mutant peptide and the wild type peptide (β-gal activity of mutant/wild type) to the putative target. For the YTH interaction assay mutants DR15PE (SEQ ID NO:2), DR15QI (SEQ ID NO:3), and DR15YM (SEQ ID NO:4) as well as originally identified DR15wt (SEQ ID NO:1), were used. The selection criteria for categorizing the interactions is shown in FIG. 8.

Based on these functional and interaction categorizations, graphic profile representations for each potential target polypeptide were obtained using a weighted categorization process as depicted in FIG. 9. In FIG. 9, the functional profile (reporter ratios of DR15wt (SEQ ID NO:1) and its three mutants) is plotted along the X-axis and the interaction profile (β-galactosidase signal from the YTH assay for DR15wt (SEQ ID NO:1) and its three mutants) is plotted along the Y-axis. The X-axis is further categorized into L (loss of function), R (reduction of function), N (functionally neutral), and I (increase of function) based on the reporter ratios. A ratio of <1.11 is categorized as an L and N includes ratios that fall within ±50% of the wild type peptide ratio. A ratio that is greater than +50% of the wt peptide ratio is I. R includes ratios greater than 1.11 and ratios less than −50% of the wt peptide ratio. Similarly, the Y-axis is further categorized based on the criteria in FIG. 8. In such a graphic profile, profiles that correspond closely have interaction values (in this case, β-galactosidase signal) and functional values (in this case, reporter ratios) that fall along a line with a positive slope. Also, close correspondence is indicated when the mutants fall within the same category type using both the reporter ratio and the β-galactosidase signal, i.e., a mutant categorized as a L based on the reporter ratio is also categorized as a L based on the β-galactosidase signal. In this case, the interaction and functional profiles for clone 3.2DR15_Y_GB_UN_0031 fall along a line with a positive slope. Each of the three mutants also fall within the same respective categories based on both reporter ratio and β-galactosidase signal. The profiles for the other putative target clones selected in the initial YTH screen do not satisfy these criteria.

Based on the close correspondence observed between the interaction and functional profiles, the polypeptide encoded by clone 3.2DR15_Y_GB_UN_0031 was identified as a target for peptide DR15wt (SEQ ID NO:1). The clone was sequenced and a sequence comparison (using a Blast search with default parameters) with sequences in the NCBI (GenBank) nucleic acid database carried out. From this sequences comparison the clone 3.2DR15_Y_GB_UN_0031 was identified as human thioredoxin-related 32 kDa protein, NCBI accession #NP_004777, encoded by NM_004786.

While the invention has been described by reference to various specific embodiments, skilled artisans will recognize that numerous modifications may be made thereto without departing from the spirit and the scope of the appended claims.

All references cited throughout the disclosure are incorporated herein by reference in their entireties for all purposes.

What is claimed is:

1. A method comprising:
   a) assaying a compound for binding to a TXNL polypeptide comprising an amino acid sequence that is at least 80% identical to the sequence of SEQ ID NO:5; and
   b) assaying said compound for modulation of IL-4 induced IgE production.

2. The method of claim 1, wherein said assaying step b) comprises assaying said compound for inhibition of IL-4 receptor mediated IgE production.

3. The method of claim 1, wherein said assaying step b) comprises assaying said compound for inhibition of IL-4 receptor mediated isotype switching of B-cells.

4. The method of claim 1, wherein said assaying step b) comprises assaying said compound for inhibition of IL-4 induced transcription of a germline ε promoter.

5. The method of claim 1, wherein said TXNL is a mammalian TXNL.

6. The method of claim 5 in which the mammalian TXNL is a human TXNL.

7. The method of claim 1, wherein said assaying step a) is a competitive binding assay.

8. The method of claim 7 in which the compound competes for binding the TXNL with an DR15 compound characterized by structural formula (I):

$$Z^1\text{—}X^1\text{~}X^2\text{~}X^3\text{~}X^4\text{~}X^5\text{~}X^6\text{~}X^7\text{~}X^8\text{~}X^9\text{~}X^{10}\text{~}X^{11}\text{~}X^{12}\text{~}X^{13}\text{~}X^{14}\text{~}X^{15}\text{~}X^{16}\text{~}X^{17}\text{~}X^{18}\text{~}X^{19}\text{~}X^{20}\text{—}Z^2$$

wherein:
   $X^1$ is a small aliphatic or a conformationally constrained residue;
   $X^2$ is a small aliphatic or an acidic residue;
   $X^3$ is a basic residue;

$X^4$ is a polar hydrophilic residue;
$X^5$ is a small aliphatic or an aromatic residue;
$X^6$ is a small aliphatic or a non-polar residue;
$X^7$ is a basic residue;
$X^8$ is a non-polar residue;
$X^9$ is a conformationally constrained residue;
$X^{10}$ is a conformationally constrained residue;
$X^{11}$ is a polar residue;
$X^{12}$ is a small polar residue;
$X^{13}$ is an aliphatic residue;
$X^{14}$ is a small aliphatic residue;
$X^{15}$ is an acidic residue;
$X^{16}$ is a small aliphatic residue;
$X^{17}$ is a polar or a small aliphatic residue;
$X^{18}$ is an aliphatic residue;
$X^{19}$ is an aromatic residue;
$X^{20}$ is a small polar residue;
$Z^1$ is RRN—, RC(O)NR—, RS(O)$_2$NR— or an amino-terminal blocking group;
$Z^2$ is —C(O)OR, —C(O)O—, —C(O)NRR or a carboxyl-terminal blocking group;
each R is independently selected from the group consisting of hydrogen, alkyl, substituted alkyl, aryl, substituted aryl, arylalkyl, substituted arylalkyl, heteroaryl, substituted heteroaryl, heteroarylalkyl and substituted heteroarylalkyl;
each "~" independently represents an amide, a substituted amide or an isostere of an amide;
each "—" represents a bond, or a 1 to 10 residue peptide or peptide analog; and
wherein one or more of $X^1$, $X^2$, $X^{19}$, or $X^{20}$ may be absent.

9. The method of claim 8 in which the active DR15 compound is selected from the group consisting of DR15wt (SEQ ID NO:1), DR15PE (SEQ ID NO:2), DR15Q1 (SEQ ID NO:3), and DR15YM (SEQ ID NO:4).

10. The method of claim 1, wherein said assaying step a) is carried out in a cell-free system using an isolated TXNL.

11. The method of claim 1 in which the compound is a small organic compound.

12. The method of claim 11 in which the small organic compound has a molecular weight in the range of about 100-2500 Dalton.

13. The method of claim 1 in which the compound is selected from the group consisting of peptides and peptide analogs.

14. A method of identifying compounds that modulate IL-4 receptor mediated IgE production, comprising:
contacting a compound from pool of candidate compounds with a TXNL polypeptide having at least 80% sequence identity to the sequence of SEQ ID NO:5,
identifying those compounds of the pool that bind the TXNL, and
assaying said compounds for modulation of IL-4 receptor mediated IgE production.

15. The method of claim 14, wherein said contacting step is carried out in the presence of a compound known to bind the TXNL such that those compounds of the pool that competitively bind the TXNL are identified.

16. The method of claim 15 in which the compound known to bind the TXNL is an DR15 compound characterized by structural formula (I):

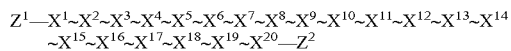

wherein:
$X^1$ is a small aliphatic or a conformationally constrained residue;
$X^2$ is a small aliphatic or an acidic residue;
$X^3$ is a basic residue;
$X^4$ is a polar hydrophilic residue;
$X^5$ is a small aliphatic or an aromatic residue;
$X^6$ is a small aliphatic or a non-polar residue;
$X^7$ is a basic residue;
$X^8$ is a non-polar residue;
$X^9$ is a conformationally constrained residue;
$X^{10}$ is a conformationally constrained residue;
$X^{11}$ is a polar residue;
$X^{12}$ is a small polar residue;
$X^{13}$ is an aliphatic residue;
$X^{14}$ is a small aliphatic residue;
$X^{15}$ is an acidic residue;
$X^{16}$ is a small aliphatic residue;
$X^{17}$ is a polar or a small aliphatic residue;
$X^{18}$ is an aliphatic residue;
$X^{19}$ is an aromatic residue;
$X^{20}$ is a small polar residue;
$Z^1$ is RRN—, RC(O)NR—, RS(O)$_2$NR— or an amino-terminal blocking group;
$Z^2$ is —C(O)OR, —C(O)O—, —C(O)NRR or a carboxyl-terminal blocking group;
each R is independently selected from the group consisting of hydrogen, alkyl, substituted alkyl, aryl, substituted aryl, arylalkyl, substituted arylalkyl, heteroaryl, substituted heteroaryl, heteroarylalkyl and substituted heteroarylalkyl;
each "~" independently represents an amide, a substituted amide or an isostere of an amide;
each "—" represents a bond, or a 1 to 10 residue peptide or peptide analog; and
wherein one or more of $X^1$, $X^2$, $X^{19}$, or $X^{20}$ may be absent.

17. The method of claim 16 in which the active DR15 compound is selected from the group consisting of DR15wt (SEQ ID NO1), DR15PE (SEQ ID NO:2), DR15Q1 (SEQ ID NO:3), and DR15YM (SEQ ID NO:4).

18. The method of claim 14 in which the candidate compounds are peptides or small organic compounds.

19. The method of claim 18 in which the pool of candidate compounds is a phage display library.

20. The method of claim 18 in which the candidate compounds are immobilized on a substrate or a plurality of substrates.

21. The method of claim 14 in which the compound or TXNL is labeled with a detectable label.

22. The method of claim 14 in which the TXNL is immobilized on a substrate.

23. The method of claim 8 in which the active DR15 compound is selected from the group consisting of compounds DR15wt (SEQ ID NO:1), DR15PE (SEQ ID NO:2), DR15Q1 (SEQ ID NO:3), and DR15YM (SEQ ID NO:4) in which one or more amide linkages of the compounds are replaced with an isostere of an amide.

24. The method of claim 16 in which the active DR15 compound is selected from the group consisting of compounds DR15wt (SEQ ID NO:1), DR15PE (SEQ ID NO:2), DR15Q1 (SEQ ID NO:3), and DR15YM (SEQ ID NO:4) in which one or more amide linkages of the compounds are replaced with an isostere of an amide.

25. The method of claim 1 in which the TXNL polypeptide is SEQ ID NO:5.

26. The method of claim 14 in which the TXNL polypeptide is SEQ ID NO:5.

27. The method of claim 1, wherein said TXNL polypeptide comprising an amino acid sequence that is at least 95% identical to the sequence of SEQ ID NO:5.

28. The method of claim 14, wherein said TXNL polypeptide comprising an amino acid sequence that is at least 95% identical to the sequence of SEQ ID NO:5.

* * * * *

SEQUENCE LISTING

<160> NUMBER OF SEQ ID NOS: 12

<210> SEQ ID NO 1
<211> LENGTH: 20
<212> TYPE: PRT
<213> ORGANISM: Artificial Sequence
<220> FEATURE:
<223> OTHER INFORMATION: peptide generated from a combinatorial library

<400> SEQUENCE: 1

Pro Glu Arg Cys Tyr Met Arg Met Pro Pro Gln Ser Leu Ala Asp Ala
1               5                   10                  15

Gln Ile Tyr Ser
            20

```
<210> SEQ ID NO 2
<211> LENGTH: 20
<212> TYPE: PRT
<213> ORGANISM: Artificial Sequence
<220> FEATURE:
<223> OTHER INFORMATION: Peptide generated by a combinatorial library

<400> SEQUENCE: 2

Ala Ala Arg Cys Tyr Met Arg Met Pro Pro Gln Ser Leu Ala Asp Ala
1               5                   10                  15

Gln Ile Tyr Ser
            20

<210> SEQ ID NO 3
<211> LENGTH: 20
<212> TYPE: PRT
<213> ORGANISM: Artificial Sequence
<220> FEATURE:
<223> OTHER INFORMATION: peptide generated from combinatorial library

<400> SEQUENCE: 3

Pro Glu Arg Cys Tyr Met Arg Met Pro Pro Gln Ser Leu Ala Asp Ala
1               5                   10                  15

Ala Ala Tyr Ser
            20

<210> SEQ ID NO 4
<211> LENGTH: 20
<212> TYPE: PRT
<213> ORGANISM: Artificial Sequence
<220> FEATURE:
<223> OTHER INFORMATION: peptide generated from combinatorial library

<400> SEQUENCE: 4

Pro Glu Arg Cys Ala Ala Arg Met Pro Pro Gln Ser Leu Ala Asp Ala
1               5                   10                  15

Gln Ile Tyr Ser
            20

<210> SEQ ID NO 5
<211> LENGTH: 289
<212> TYPE: PRT
<213> ORGANISM: Homo sapiens

<400> SEQUENCE: 5

Met Val Gly Val Lys Pro Val Gly Ser Asp Pro Asp Phe Gln Pro Glu
1               5                   10                  15

Leu Ser Gly Ala Gly Ser Arg Leu Ala Val Val Lys Phe Thr Met Arg
                20                  25                  30

Gly Cys Gly Pro Cys Leu Arg Ile Ala Pro Ala Phe Ser Ser Met Ser
            35                  40                  45

Asn Lys Tyr Pro Gln Ala Val Phe Leu Glu Val Asp Val His Gln Cys
        50                  55                  60

Gln Gly Thr Ala Ala Thr Asn Asn Ile Ser Ala Thr Pro Thr Phe Leu
65                  70                  75                  80

Phe Phe Arg Asn Lys Val Arg Ile Asp Gln Tyr Gln Gly Ala Asp Ala
                85                  90                  95

Val Gly Leu Glu Glu Lys Ile Lys Gln His Leu Glu Asn Asp Pro Gly
                100                 105                 110

Ser Asn Glu Asp Thr Asp Ile Pro Lys Gly Tyr Met Asp Leu Met Pro
```

```
                115                 120                 125
        Phe Ile Asn Lys Ala Gly Cys Glu Cys Leu Asn Glu Ser Asp Glu His
                    130                 135                 140

Gly Phe Asp Asn Cys Leu Arg Lys Asp Thr Thr Phe Leu Glu Ser Asp
        145                 150                 155                 160

Cys Asp Glu Gln Leu Leu Ile Thr Val Ala Phe Asn Gln Pro Val Lys
                        165                 170                 175

Leu Tyr Ser Met Lys Phe Gln Gly Pro Asp Asn Gly Gln Gly Pro Lys
                    180                 185                 190

Tyr Val Lys Ile Phe Ile Asn Leu Pro Arg Ser Met Asp Phe Glu Glu
                195                 200                 205

Ala Glu Arg Ser Glu Pro Thr Gln Ala Leu Glu Leu Thr Glu Asp Asp
            210                 215                 220

Ile Lys Glu Asp Gly Ile Val Pro Leu Arg Tyr Val Lys Phe Gln Asn
        225                 230                 235                 240

Val Asn Ser Val Thr Ile Phe Val Gln Ser Asn Gln Gly Glu Glu Glu
                        245                 250                 255

Thr Thr Arg Ile Ser Tyr Phe Thr Phe Ile Gly Thr Pro Val Gln Ala
                    260                 265                 270

Thr Asn Met Asn Asp Phe Lys Arg Val Val Gly Lys Lys Gly Glu Ser
                275                 280                 285

His

<210> SEQ ID NO 6
<211> LENGTH: 603
<212> TYPE: DNA
<213> ORGANISM: Homo sapiens

<400> SEQUENCE: 6
ctcgaggaca gtgacctggg agtgagtaca aggtgaggcc accactcagg gtgccagctc    60
caagcgggtc acagggacga gggctgcggc catcaggagg ccctgcacac acatctggga   120
cacgcgcccc cgagggccag ttcacctcag tgcgcctcat tctcctgcac aaaagcgccc   180
ccatcctttc ttcacaaggc tttcgtggaa gcagaggcgt cgatgccag tacctctcc    240 ctttcccagg caacgggacc ccaagtttgc tgactgggac caccaagcca cgcatgcgtc   300
aagagtgaga gtccgggacc taggcagggg ccctgggtt gggcctgaga gagaagagaa   360
cctcccccag cactcggtgt gcatcggtag tgaaggagcc tcacctgacc ccgctgttg   420 ctcaatcgac ttcccaagaa cagagagaaa agggaacttc cagggcggcc cgggcctcct   480
gggggttccc accccatttt tagctgaaag cactgaggca gagctccccc tacccaggct   540
ccactgcccg gcacagaaat aacaaccacg gttactgatc atctgggagc tgtccaggaa   600
ttc                                                                  603

<210> SEQ ID NO 7
<211> LENGTH: 20
<212> TYPE: DNA
<213> ORGANISM: Artificial Sequence
<220> FEATURE:
<223> OTHER INFORMATION: pcr primer

<400> SEQUENCE: 7
atccacaggc accaaatgga                                                 20

<210> SEQ ID NO 8
<211> LENGTH: 19
```

```
<212> TYPE: DNA
<213> ORGANISM: Artificial Sequence
<220> FEATURE:
<223> OTHER INFORMATION: pcr primer

<400> SEQUENCE: 8
ggaagacgga tgggctctg                                                    19

<210> SEQ ID NO 9
<211> LENGTH: 20
<212> TYPE: DNA
<213> ORGANISM: Artificial Sequence
<220> FEATURE:
<223> OTHER INFORMATION: DNA probe

<400> SEQUENCE: 9
acccggcgct tcagcctcca                                                   20

<210> SEQ ID NO 10
<211> LENGTH: 15
<212> TYPE: DNA
<213> ORGANISM: Artificial Sequence
<220> FEATURE:
<223> OTHER INFORMATION: pcr primer

<400> SEQUENCE: 10
cagcactgcg ggccc                                                        15

<210> SEQ ID NO 11
<211> LENGTH: 18
<212> TYPE: DNA
<213> ORGANISM: Artificial Sequence
<220> FEATURE:
<223> OTHER INFORMATION: pcr primer

<400> SEQUENCE: 11
tcagcgggaa gaccttgg                                                     18

<210> SEQ ID NO 12
<211> LENGTH: 22
<212> TYPE: DNA
<213> ORGANISM: Artificial Sequence
<220> FEATURE:
<223> OTHER INFORMATION: DNA probe

<400> SEQUENCE: 12
ccagcagcct gaccagcatc cc                                                22
```